(12) United States Patent
Keyes et al.

(10) Patent No.: US 8,207,350 B2
(45) Date of Patent: Jun. 26, 2012

(54) ACETYL-CoA CARBOXYLASE (ACC) INHIBITORS AND THEIR USE IN DIABETES, OBESITY AND METABOLIC SYNDROME

(75) Inventors: Robert F. Keyes, Pleasant Prairie, WI (US); Yu Gui Gu, Libertyville, IL (US); Hing L. Sham, South San Francisco, CA (US)

(73) Assignee: Abbott Laboratories, Abbott Park, IL (US)

( * ) Notice: Subject to any disclaimer, the term of this patent is extended or adjusted under 35 U.S.C. 154(b) by 581 days.

(21) Appl. No.: 12/259,090

(22) Filed: Oct. 27, 2008

(65) Prior Publication Data

US 2009/0048298 A1 Feb. 19, 2009

Related U.S. Application Data

(63) Continuation of application No. 11/675,426, filed on Feb. 15, 2007, now abandoned.

(60) Provisional application No. 60/773,440, filed on Feb. 15, 2006.

(51) Int. Cl.
*A61K 31/428* (2006.01)
*C07D 277/64* (2006.01)
*C07D 277/74* (2006.01)
(52) U.S. Cl. ........................ 548/165; 514/367
(58) Field of Classification Search .................. 548/165
See application file for complete search history.

(56) References Cited

U.S. PATENT DOCUMENTS

| 2004/0176409 A1 | 9/2004 | McGee et al. |
| 2005/0203146 A1 | 9/2005 | Herpin et al. |

FOREIGN PATENT DOCUMENTS

| WO | 02051355 | 7/2002 |
| WO | 2005044793 | 5/2005 |
| WO | 2005070920 | 8/2005 |
| WO | 2005113069 | 12/2005 |

OTHER PUBLICATIONS

Turkoglu et al., "Effect of Abdominal Obesity on Insulin Resistance and the Components of the Metabolics Syndrome: Evidence Supporting Obesity as the Central Feature" Obes. Surg. 13: 699-705 (2003).
Steyn et al., "Diet, Nutrition and the Prevention of Type 2 Diabetes" Public Health Nutr. 7: 146-165 (2004).
Hulver et al., "Skeletal Muscle Lipid Metabolism with Obesity" Am. J. Physiol. Endocrinol Metab. 284: E741-747 (2003).
Sinha, et al., "Assessment of Skeletal Muscle Triglyceride Content by 1H Nuclear Magnetic Resonance Spectroscopy in Lean and Obese Adolescents: Relationships to Insulin Sensitivity, Total Body Fat, and Central Adiposity" Diabetes 51: 1022-1027 (2002).
Friedman et al., "Fat in All the Wrong Places" Nature 415: 268-269 (2002).
Ruderman et al., "AMP Kinase and Malonyl-CoA: Targets for Therapy of the Metabolic Syndrome" Nature Rev. Drug Discov. 3: 340-351 (2004).
Mao et al., "Human Acetyl-CoA Carboxylase 1 Gene: Presence of Three Promoters and Heterogeneity at the 5-untranslated mRNA region" Proc. Natl. Acad. Sci. USA 100: 7515-7520 (2003).
Abu-Elheiga et al., "Continuous Fatty Acid Oxidation and Reduced Fat Storage in Mice Lacking Acetyl-CoA Carboxylase 2" Science 291: 2613-2616 (2001).
Abu-Elheiga et al., "Acetyl-CoA Carboxylase 2 Mutant Mice are Protected Against Obesity and Diabetes Induced by High-Fat/High-Carbohydrate Diets" Proc. Natl. Acad. Sci. USA 100: 10207-10212 (2003).
Yamauchi et al., "The Fat-derived Hormone Adiponectin Reverses Insulin Resistance Associated with Both Lipoatrophy and Obesity" Nat. Med. 7: 941-946 (2001).
Higuchi and Stella, Pro-drugs as Novel Delivery Systems, vol. 14 of the A.C.S. Symposium Series, Table of Contents, (1975).
Roche, Bioreversible Carriers in Drug Design, American Pharmaceutical Association and Pergamon Press, Table of Contents (1987).
Abu-Elheiga et al., "The Subcellular Localization of Acetyl-CoA Carboxylase 2" Proc. Natl. Acad. Sci. USA 97: 1444-1449 (2000).
Abu-Elheiga et al., "Human Acetyl-CoA Carboxylase 2: Molecular Cloning, Characterization, Chromosomal Mapping, and Evidence for Two Isoforms" J. Biol. Chem. 272: 10669-10677 (1997).
Greene, T.W. et al., Protective Groups in Organic Synthesis, 3rd Edition, John Wiley & Sons, Inc. Table of Contents (1999).

*Primary Examiner* — Laura L. Stockton
(74) *Attorney, Agent, or Firm* — Lisa V. Mueller; Michael Best & Friedrich LLP

(57) ABSTRACT

The present invention relates to compounds of formula (I)

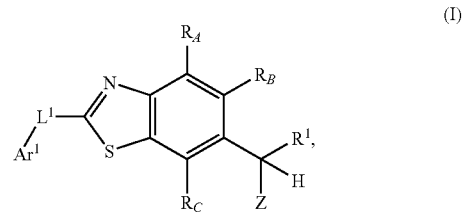

which inhibit acetyl-CoA carboxylase (ACC) and are useful for the prevention or treatment of metabolic syndrome, type II diabetes, obesity, atherosclerosis and cardiovascular diseases in humans.

25 Claims, No Drawings

ACETYL-COA CARBOXYLASE (ACC) INHIBITORS AND THEIR USE IN DIABETES, OBESITY AND METABOLIC SYNDROME

CROSS-REFERENCE SECTION TO RELATED APPLICATIONS

This application is a continuation of U.S. patent application Ser. No. 11/675,426 filed on Feb. 15, 2007; which claims the benefit of priority to U.S. Provisional Patent Application Ser. No. 60/773,440, filed on Feb. 15, 2006, all of which are incorporated herein by reference.

FIELD OF THE INVENTION

The present invention relates to compounds, which inhibit acetyl-CoA carboxylase (ACC) and are useful for the prevention or treatment of metabolic syndrome, type 2 diabetes, obesity, atherosclerosis and cardiovascular diseases in humans.

BACKGROUND OF THE INVENTION

The incidence of type 2 diabetes has dramatically increased over the past decade. This epidemic is largely attributed to proliferation of key risk factors, which include a sedentary lifestyle, a high fat diet, obesity and the demographic shift to a more aged population. There is ample evidence to indicate that increased abdominal obesity and physical inactivity contribute significantly to the development of type 2 diabeties (Turkoglu C, Duman B S, Gunay D, Cagatay P, Ozcan R, Buyukdevrim A S: Effect of abdominal obesity on insulin resistance and the components of the metabolic syndrome: evidence supporting obesity as the central feature. Obes Surg 2003; 13: 699-705. Steyn N P, Mann J, Bennett P H, Temple N, Zimmet P, Tuomilehto J, Lindstrom J, Louheranta A: Diet, nutrition and the prevention of type 2 diabetes. Public Health Nutr 2004; 7: 147-65).

At the cellular level, an increase in ectopic fat storage in nonadipose tissues such as in muscle, liver and pancreas is a strong predictor of the development of insulin resistance and type 2 diabeties (Hulver M W, Berggren J R, Cortright R N, Dudek R W, Thompson R P, Pories W J, MacDonald K G, Cline G W, Shulman G I, Dohm G L, Houmard J A: Skeletal muscle lipid metabolism with obesity. Am J Physiol Endocrinol Metab 2003; 284: E741-7. Sinha R, Dufour S, Petersen K F, LeBon V, Enoksson S, Ma Y Z, Savoye M, Rothman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity. Diabetes 2002; 51: 1022-7). The precise mechanism of how increased intracellular lipid content exacerbates whole body insulin sensitivity is unclear at present but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production (Sinha R, Dufour S, Petersen K F, LeBon V, Enoksson S, Ma Y Z, Savoye M, Rothman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity. Diabetes 2002; 51: 1022-7. Friedman J: Fat in all the wrong places. Nature 2002; 415: 268-9). As muscle is the primary site of metabolic action of insulin, the development of muscle insulin resistance along with liver insulin resistance are thus inherently linked to the development of whole body insulin resistance.

In order to increase muscle and liver fat oxidation and thus limit the concentration of LCFACoA's we aim to inhibit the activity of Acetyl CoA Carboxylase (ACC), which catalyzes the production of malonyl-CoA from acetyl-CoA. Malonyl-CoA is an intermediate substrate that plays an important role in the overall fatty acid metabolism: Malonyl-CoA is utilized by fatty acid synthase for de novo lipogenesis, and also acts as a potent allosteric inhibitor of carnitine palmitoyltransferase 1 (CPT1), a mitochondrial membrane protein that shuttles long chain fatty acyl CoAs into the mitochondrial where they are oxidized (Ruderman N, Prentki M: AMP kinase and malonyl-CoA: targets for therapy of the metabolic syndrome. Nat Rev Drug Discov 2004; 3: 340-51). A small molecule inhibitor of ACC would thus limit de novo lipid synthesis, de-inhibit CPT1 and subsequently increase fat oxidation.

In rodents and in humans, there are two known isoforms of ACC that are encoded by distinct genes and share approximately 70% amino acids identity. ACC1, which encodes a 265 KD protein, is highly expressed in the cytosol of lipogenic tissues such as liver and adipose, whereas 280 KD ACC2 protein is preferentially expressed in oxidative tissues, skeletal muscle and heart (Mao J, Chirala S S, Wakil S J: Human acetyl-CoA carboxylase 1 gene: presence of three promoters and heterogeneity at the 5'-untranslated mRNA region. Proc Natl Acad Sci USA 2003; 100: 7515-20. Abu-Elheiga L, Almarza-Ortega D B, Baldini A, Wakil S J: Human acetyl-CoA carboxylase 2. Molecular cloning, characterization, chromosomal mapping, and evidence for two isoforms. J Biol Chem 1997; 272: 10669-77). ACC2 has a unique 114 amino acid N-terminus with a putative transmembrane domain (TM), which is thought to be responsible for mitochondrial targeting (Abu-Elheiga L, Brinkley W R, Zhong L, Chirala S S, Woldegiorgis G, Wakil S J: The subcellular localization of acetyl-CoA carboxylase 2. Proc Natl Acad Sci USA 2000; 97: 1444-9). Based on tissue distribution and subcellular localization of these two isoforms, the current hypothesis is that a distinct pool of Malonyl-CoA produced by ACC1 is preferentially converted into fatty acids by fatty acid synthase, whereas another pool of Malonyl-CoA synthesized primarily by ACC2, presumed localized in near mitochondria, can be involved in the inhibition of CPT1 (Abu-Elheiga L, Brinkley W R, Zhong L, Chirala S S, Woldegiorgis G, Wakil S J: The subcellular localization of acetyl-CoA carboxylase 2. Proc Natl Acad Sci USA 2000; 97: 1444-9). Therefore, ACC1 inhibition reduces fatty acid synthesis and can be beneficial for use in treating diseases such as metabolic syndrome.

Genetic studies have demonstrated that ACC2 knockout mice are healthy and fertile with a favorable metabolic phenotype, increased fatty acid oxidation, increased thermogenesis, reduced hepatic TG content and subsequent decrease in body weight despite increase in food intake compared to their littermates (Abu-Elheiga L, Matzuk M M, Abo-Hashema K A, Wakil S J: Continuous fatty acid oxidation and reduced fat storage in mice lacking acetyl-CoA carboxylase 2. Science 2001; 291: 2613-6). In addition, these mice are resistant against high fat diet-induced obesity and insulin resistance (Abu-Elheiga L, Oh W, Kordari P, Wakil S J: Acetyl-CoA carboxylase 2 mutant mice are protected against obesity and diabetes induced by high-fat/high-carbohydrate diets. Proc Natl Acad Sci USA 2003; 100: 10207-12). Also, recently it was demonstrated that the effects of leptin and adiponectin, cytokines secreted from adipose tissue, to increase fatty acid oxidation are at least due in part to the inhibition of ACC in liver and skeletal muscle (Yamauchi T, Kamon J, Waki H, Terauchi Y, Kubota N, Hara K, Mori Y, Ide T, Murakami K, Tsuboyama-Kasaoka N, Ezaki O, Akanuma Y, Gavrilova O, Vinson C, Reitman M L, Kagechika H, Shudo K, Yoda M, Nakano Y, To be K, Nagai R, Kimura S, Tomita M, Froguel P, Kadowaki T: The fat-derived hormone adiponectin reverses insulin resistance associated with both lipoatrophy and obesity. Nat Med 2001; 7: 941-6). Taken together these data support that the discovery of small molecular inhibitors of ACC2 can provide a favorable metabolic profile against obesity induced type 2 diabetic patients. Furthermore, the dual inhibition of ACC1 and ACC2 can provide the profile needed to demonstrate benefit for patients exhibiting conditions of metabolic syndrome.

SUMMARY OF THE INVENTION

The present invention is directed to compounds of formula (I), or a pharmaceutical acceptable salt, prodrug, salt of a prodrug, or a combination thereof,

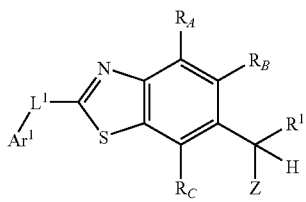

(I)

wherein $R_1$ is hydrogen, alkyl, haloalkyl, or cycloalkyl;

$L^1$ is —$CR_xR_y$—, —C(O)—, —O—, —S—, —N(alkyl)-, or —N(H)—; wherein each of $R_x$ and $R_y$ is independently selected from the group consisting of hydrogen, alkyl, hydroxyalkyl and haloalkyl; or $R_x$ and $R_y$ together with the carbon to which they are attached form a three to six-membered monocyclic ring selected from the group consisting of cycloalkyl and heterocycle ring;

$R_A$, $R_B$ and $R_C$ are each independently hydrogen, alkyl, halogen or haloalkyl;

Z is —CN, —$OR^2$, -alkylenyl-$OR^2$, —$N(R^3)(R^4)$ or -alkylenyl-$N(R^3)(R^4)$;

$R^2$, at each occurrence, is independently selected from the group consisting of hydrogen, alkyl, haloalkyl, —C(O)$OR_a$, —S(O)$_2R_a$, —C(O)N($R_a$)($R_b$), —S(O)$_2$N($R_a$)($R_b$), —C(O)$R_a$, -alkylenyl-$OR_a$, -alkylenyl-N($R_a$)($R_b$), -alkylenyl-N($R_b$)C(O)$OR_a$, -alkylenyl-N($R_b$)C(O)N($R_a$)($R_b$), -alkylenyl-N($R_b$)C(O)$R_a$, -alkylenyl-N($R_b$)S(O)$_2R_a$, -alkylenyl-C(O)$OR_a$, -alkylenyl-S(O)$_2R_a$, -alkylenyl-S(O)$_2OR_a$, -alkylenyl-S(O)$_2$N($R_a$)($R_b$), -alkylenyl-C(O)N($R_a$)($R_b$) and -alkylenyl-C(O)$R_a$;

$R^3$, at each occurrence, is independently selected from the group consisting of hydrogen, alkyl and haloalkyl;

$R^4$, at each occurrence, is independently selected from the group consisting of hydrogen, alkyl, hydroxy, alkoxy, —C(=NH)NH$_2$, —C(O)$OR_a$, —S(O)$_2R_a$, —C(O)N($R_a$)($R_b$), S(O)$_2$N($R_a$)($R_b$), —C(O)$R_a$, —C(O)CH$_2$C(O)$R_a$, haloalkyl, -alkylenyl-$OR_a$, -alkylenyl-N($R_a$)($R_b$), -alkylenyl-N($R_b$)C(O)$OR_a$, -alkylenyl-N($R_b$)C(O)N($R_a$)($R_b$), -alkylenyl-N($R_b$)S(O)$_2R_a$, -alkylenyl-N($R_b$)C(O)$R_3$, -alkylenyl-C(O)$OR_a$, -alkylenyl-S(O)$_2R_a$, -alkylenyl-S(O)$_2OR_a$, -alkylenyl-S(O)$_2$N($R_a$)($R_b$), -alkylenyl-C(O)N($R_a$)($R_b$) and -alkylenyl-C(O)$R_a$, $Ar^1$ is phenyl or monocyclic heteroaryl, each of which is optionally fused to a phenyl or a monocyclic, five- or six-membered ring selected from the group consisting of cycloalkyl, cycloalkenyl, heterocycle and heteroaryl, and each $Ar^1$ is independently unsubstituted or substituted with 1, 2, 3 or 4 substituents independently selected from the group consisting of alkyl, alkenyl, —CN, —NO$_2$, halogen, —$OR^6$, —O—N=CH($R^5$), —OC(O)$R^5$, —OC(O)N($R^7$)($R^6$), —OC(O)$OR^5$, —OS(O)$_2R^5$, —$SR^6$, —S(O)$R^5$, —S(O)$_2R^5$, —S(O)$_2OR^6$, —S(O)$_2$N($R^7$)($R^6$), —C(O)$R^6$, —C(O)N($R^7$)($R^6$), —C(O)$OR^6$, —C(O)N($R^7$)($R^6$), —N($R^7$)($R^6$), —N(H)—N=CH($R^5$), —N($R^7$)C(O)$R^6$, —N($R^7$)C(O)$OR^6$, —N($R^7$)S(O)$_2R^6$, —N($R^7$)C(O)N($R^7$)($R^6$), —N($R^7$)S(O)$_2$N($R^7$)($R^6$), —$R^8$, haloalkyl, cyanoalkyl, nitroalkyl, hydroxyalkyl, alkoxyalkyl, haloalkoxyalkyl, -alkylenyl-OC(O)$R^5$, -alkylenyl-OC(O)N($R^7$)($R^6$), -alkylenyl-OC(O)$OR^5$, -alkylenyl-OS(O)$_2R^5$, -alkylenyl-$SR^6$, -alkylenyl-S(O)$R^5$, -alkylenyl-S(O)$_2R^5$, -alkylenyl-S(O)$_2OR^6$, -alkylenyl-S(O)$_2$N($R^7$)($R^6$), -alkylenyl-C(O)$R^6$, -alkylenyl-C(O)N($R^7$)($R^6$), -alkylenyl-C(O)$OR^6$, -alkylenyl-C(O)N($R^7$)($R^6$), -alkylenyl-N($R^7$)($R^6$), -alkylenyl-N($R^7$)C(O)$R^5$, -alkylenyl-N($R^7$)C(O)$OR^5$, -alkylenyl-N($R^7$)S(O)$_2R^5$, -alkylenyl-N($R^7$)C(O)N($R^7$)($R^6$), -alkylenyl-N($R^7$)S(O)$_2$N($R^7$)($R^6$), and -alkylenyl-$R^8$;

$R^5$, at each occurrence, is independently selected from the group consisting of alkyl, alkenyl, haloalkyl, alkoxyalkyl, haloalkoxyalkyl, —$R^8$, and -alkylenyl-$R^8$;

$R^6$, at each occurrence, is independently selected from the group consisting of hydrogen, alkyl, alkenyl, haloalkyl, alkoxyalkyl, haloalkoxyalkyl, —$R^8$, and -alkylenyl-$R^8$;

$R^7$, at each occurrence, is independently selected from the group consisting of hydrogen, alkyl, arylalkyl, haloalkyl, and heteroarylalkyl;

$R^8$, at each occurrence, is independently selected from the group consisting of aryl, heteroaryl, heterocycle, cycloalkyl and cycloalkenyl;

the phenyl, cycloalkyl, cycloalkenyl, aryl, heteroaryl, heterocycle, aryl moiety of the arylalkyl, and the heteroaryl moiety of the heteroarylalkyl represented by $R^7$ and $R^8$, are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —$OR_a$, —OC(O)$R_a$, —OC(O)$OR_a$, —OS(O)$_2R_a$, —S(alkyl), —S(O)alkyl, —S(O)$_2$alkyl, —S(O)$_2OR_a$, —S(O)$_2$N$R_aR_b$, —C(O)$R_a$, —C(O)N$R_aR_b$, —C(O)$OR_a$, —C(O)N$R_aR_b$, —N$R_aR_b$, —NO$R_a$, —N($R_b$)C(O)$R_a$, —N($R_b$)C(O)$OR_a$, —N($R_b$)S(O)$_2R_a$, —N($R_b$)C(O)N$R_aR_b$, —N($R_b$)S(O)$_2$N$R_aR_b$, haloalkyl, cyanoalkyl, nitroalkyl, hydroxyalkyl, alkoxyalkyl, haloalkoxyalkyl, -alkylenyl-OC(O)$R_a$, -alkylenyl-OC(O)$OR_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2OR_a$, -alkylenyl-S(O)$_2$N$R_aR_b$, -alkylenyl-C(O)$R_a$, -alkylenyl-C(O)N$R_aR_b$, -alkylenyl-C(O)$OR_a$, -alkylenyl-C(O)N$R_aR_b$, -alkylenyl-N$R_aR_b$, -alkylenyl-N($R_b$)C(O)$R_a$, -alkylenyl-N($R_b$)C(O)$OR_a$, -alkylenyl-N($R_b$)S(O)$_2R_a$, -alkylenyl-N($R_b$)C(O)N$R_aR_b$, and -alkylenyl-N($R_b$)S(O)$_2$N$R_aR_b$;

$R_a$ at each occurrence is independently selected from the group consisting of hydrogen, alkyl, alkenyl and haloalkyl, and $R_b$ at each occurrence is independently selected from the group consisting of hydrogen and alkyl.

The invention is also directed to the pharmaceutical compositions including compounds of the invention. Such compositions can be administered in accordance with a method of the invention, typically as part of a therapeutic regimen for treatment or prevention of conditions and disorders related to ACC. Another aspect of the invention relates to a method of inhibiting ACC activity. The method is useful for treating, or preventing conditions and disorders related to ACC in mammals. More particularly, the method is useful for treating or preventing conditions and disorders related to metabolic syndrome, type TI diabetes, obesity, atherosclerosis and cardiovascular diseases in mammals. Accordingly, the compounds and compositions of the invention are useful as a medicament for treating or preventing disease modulated by ACC. Processes for making compounds of the invention also are contemplated. Finally, the compounds, compositions including the compounds, methods for making the compounds, and methods for treating or preventing conditions and disorders by administering the compounds are further described herein.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

Certain terms as used in the specification are intended to refer to the following definitions, as detailed below.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkoxyalkyl" as used herein, means an alkyl group, as defined herein, in which one or two hydrogen atoms are replaced by alkoxy groups, as defined herein. Representative examples of alkoxyalkyl include, but are not limited to, methoxymethyl and ethoxymethyl.

The term "alkyl" as used herein, means a straight or branched chain hydrocarbon containing from 1 to 10 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylenyl" as used herein, means a divalent group derived from a straight or branched chain hydrocarbon of from 1 to 6 carbon atoms. Representative examples of alkylenyl include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, and 5,6,7,8-tetrahydronaphthalenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cyano" as used herein, means —CN.

The term "cyanoalkyl" as used herein, means an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, means a monocyclic or bicyclic cycloalkyl. The monocyclic cycloalkyl has three to eight carbon atoms, zero heteroatom and zero double bond. The monocyclic cycloalkyl can be attached to the parent molecular moiety through any substitutable atom contained within the monocyclic cycloalkyl. Examples of monocyclic cycloalkyls include, but are not limited to, cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl. The bicyclic cycloalkyl can be attached to the parent molecular moiety through any substitutable atom contained within the bicyclic cycloalkyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl, Representative examples of monocyclic cycloalkenyl groups include, but not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The bicyclic cycloalkenyl can be attached to the parent molecular moiety through any substitutable atom contained within the bicyclic cycloalkenyl. Representative examples of the bicyclic cycloalkenyl groups include, but not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "ethylenedioxy" as used herein, means a —O—(CH$_2$)$_2$—O— group wherein the oxygen atoms of the ethylenedioxy group are attached to two adjacent carbon atoms of the parent molecular moiety, forming a six membered ring with the parent molecular moiety.

The term "halo" or "halogen" as used herein, means —Cl, —Br, —I or —F.

The term "haloalkoxy" as used herein, means an alkoxy group, as defined herein, in which one, two, three or four hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkoxyalkyl" as used herein, means a haloalkoxy group, as defined herein, appended to the parent moiety through an alkyl group, as defined herein.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, difluoromethyl, trifluoromethyl, pentafluoroethyl, and 2-chloro-3-fluoropentyl.

The term "heterocycle" or "heterocyclic" as used herein, means a monocyclic heterocycle or a bicyclic heterocycle. The monocyclic heterocycle is a three-, four-, five-, six- or seven-membered ring containing at least one heteroatom independently selected from the group consisting of O, N, and S, in addition to the carbon within the ring. The three- or four membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle connects to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodithiolyl, benzopyranyl, benzothiopyranyl, 2,3-dihydrobenzofuranyl, 2,3-dihydrobenzothienyl, 2,3-dihydro-1H-indolyl, 2,3-dihydroisoindol-2-yl, 2,3-dihydroisoindol-3-yl, 1,3-dioxo-1H-isoindolyl, 2-(trifluoromethyl)-5,6-dihydroimidazo-[1,2-a]pyrazin-7(8H)-yl, 1-acetyl-2,3-dihydro-1H-indol-6-yl, 3-(trifluoromethyl)-5,6-dihydro[1,2,4]triazolo[4,3-a]pyrazin-7(8H)-yl, 1,2,3,4-tetrahydroisoquinolin-2-yl, and 1,2,3,4-tetrahydroquinolinyl. The monocyclic and bicyclic heterocycle of the present invention can be unsubstituted or substituted.

The term "heteroaryl" as used herein, means a monocyclic heteroaryl or a bicyclic heteroaryl. The monocyclic heteroaryl is a five- or six-membered ring. The five-membered ring consists of two double bonds, and one sulfur, nitrogen or oxygen atom, and four carbons. Alternatively, the five-membered ring has two double bonds, two, three or four nitrogen atoms and optionally one oxygen or one sulfur atom, and the others are carbon. The six-membered ring consists of three double bonds and one, two, or three nitrogen atoms, and the others are carbon. The monocyclic heteroaryl connects to the parent molecular moiety through any substitutable atom contained within the monocyclic heteroaryl. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl. The bicyclic heteroaryl connects to the parent molecular moiety through any carbon atom or any nitrogen atom contained within the bicyclic heteroaryl. Representative examples of bicyclic heteroaryl groups include, but not limited to, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, and 5,6,7,8-tetrahydroquinolin-5-yl. The monocyclic and bicyclic heteroaryl groups of the present invention can be substituted or unsubstituted.

The term "heteroarylalkyl" as used herein, refers to a heteroaryl group, as defined herein, appended to the parent molecular moiety through an alkyl group, as defined herein. Representative examples of heteroarylalkyl include, but not limited to, pyridinylmethyl, thienylethyl, thiadiazolylmethyl.

The term "heteroatom" as used herein, refers to nitrogen, oxygen or sulfur atom.

The term "hydroxy" or "hydroxyl" as used herein, means an —OH group.

The term "hydroxyalkyl" as used herein, means an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "methylenedioxy" as used herein, means a —O—(CH$_2$)—O— group wherein the oxygen atoms of the methylenedioxy group are attached to two adjacent carbon atoms of the parent molecular moiety, forming a five membered ring with the parent molecular moiety.

The term "nitro" as used herein, refers to an —NO$_2$ group.

The term "nitroalkyl" as used herein, means a nitro group, as defined herein, appended to the parent moiety through an alkyl group, as defined herein.

The term "oxo" as used herein, means =O.

Compounds of the invention can have the formula (I) as described in the summary of the invention.

In compounds of formula (I), $R^1$ is hydrogen, alkyl, haloalkyl or cycloalkyl. Particularly, $R^1$ is $C_1$-$C_6$ alkyl or $C_1$-$C_6$ haloalkyl. More particularly, $R_1$ is methyl or trifluoromethyl. Preferably, $R_1$ is methyl.

$L^1$ is —CR$_x$R$_y$—, —C(O)—, —O—, —S—, —N(alkyl)-, or —N(H)—, wherein R$_x$ and R$_y$ are as described in the summary of the invention. Particularly $L^1$ is —CH$_2$—, —C(O)—, —O—, —N(H)—, —N(alkyl)- or —S—. Preferably, $L^1$ is —O—.

$R_A$, $R_B$ and $R_C$ are each independently hydrogen, alkyl, halogen or haloalkyl. Particularly, $R_A$, $R_B$ and $R_C$ are each independently hydrogen, $C_1$-$C_6$ alkyl, I, Br, Cl, F or $C_1$-$C_6$ haloalkyl. More particularly, $R_A$, $R_B$ and $R_C$ are hydrogen.

Z is —CN, —OR$^2$, -alkylenyl-OR$^2$, —N(R$^3$)(R$^4$) or -alkylenyl-N(R$^3$)(R$^4$) wherein $R^1$, $R^2$ and $R^4$ are as described in the summary of the invention. Particularly, Z is —CN, —OR$^2$, -alkylenyl-OR$^2$, —N(R$^3$)(R$^4$) or -alkylenyl-N(R$^3$)(R$^4$) wherein $R^2$ is hydrogen or —C(O)R$_a$, $R^3$ is hydrogen and $R^4$ is hydrogen, —C(O)R$_a$, or —C(O)N(R$_a$)(R$_b$) and wherein R$_a$ and R$_b$ are as described in the summary of the invention. More particularly, Z is —CN, —OR$^2$, —N(R$^3$)(R$^4$) or —C$_1$-C$_6$ alkylenyl-N(R³)(R⁴) wherein R² is hydrogen or —C(O)R$_a$ wherein R$_a$ is C₁-C₆ alkyl, R³ is hydrogen and R⁴ is hydrogen, —C(O)R$_a$ or —C(O)N(R$_a$)(R$_b$) wherein R$_a$ is hydrogen and R$_b$ is hydrogen or C₁-C₆ alkyl. Preferably, Z is —CN, —OR², —N(R³)(R⁴) or —CH₂—N(R³)(R⁴) wherein R² is hydrogen or —C(O)R$_a$ wherein R$_a$ is methyl, R³ is hydrogen and R⁴ is hydrogen, —C(O)R$_a$ or —C(O)N(R$_a$)(R$_b$) wherein R$_a$ is hydrogen and R$_b$ is hydrogen or methyl.

Ar¹ is phenyl or monocyclic heteroaryl, each of which is optionally fused to a phenyl or a monocyclic, five- or six-membered ring selected from the group consisting of cycloalkyl, cycloalkenyl, heterocycle and heteroaryl wherein each Ar¹ is independently unsubstituted or substituted with substituents as described in the summary of the invention. Particularly, Ar¹ is unsubstituted phenyl or unsubstituted pyridinyl, each of which is fused to an unsubstituted phenyl or unsubstituted pyridinyl; or Ar¹ is a group of formula (a), (b), (c) or (d)

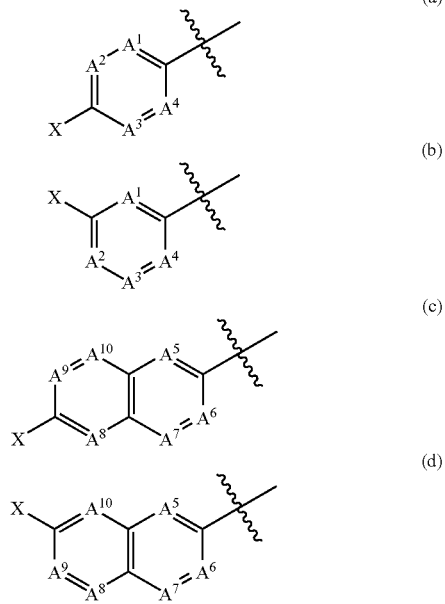

wherein

X is —OR⁶ or —N(R⁷)(R⁶) wherein R⁶ and R⁷ are as described in the summary of the invention. Particularly, X is —OR⁶ wherein R⁶ is alkyl, aryl or heteroaryl, or X is —N(R⁷)(R⁶) wherein R⁷ is hydrogen and R⁶ is aryl or heteroaryl, wherein the aryl and heteroaryl as represented by R⁶ are each independently unsubstituted or substituted with substituents as described in the summary of the invention. More particularly, X is —OR⁶ wherein R⁶ is C₁-C₆ alkyl or aryl, or X is —N(R⁷)(R⁶) wherein R⁷ is hydrogen and R⁶ is aryl, wherein the aryl as represented by R⁶ is independently unsubstituted or substituted with substituents as described in the summary of the invention. Preferably, X is —OR⁶ wherein R⁶ is C₁-C₆ alkyl, unsubstituted aryl, or aryl substituted with one C₁-C₆ alkoxy, or X is —N(R⁷)(R⁶) wherein R⁷ is hydrogen and R⁶ is aryl, unsubstituted or substituted with one C₁-C₆ alkoxy. More preferably, X is —OR⁶ wherein R⁶ is methyl, isopropy, phenyl or naphthyl, wherein the phenyl and naphthyl are independently unsubstituted or substituted with one isopropoxy, or X is —N(R⁷)(R⁶) wherein R⁷ is hydrogen and R⁶ is phenyl or naphthy, wherein the phenyl and naphthyl are independently unsubstituted or substituted with one isopropoxy.

A¹, A², A³, A⁴ are —C(R$_E$)—, or one or two of A¹, A², A³, A⁴ is N and the others are —C(R$_E$)—, A⁵, A⁶, and A⁷ are —C(R$_F$)—, or one or two of A⁵, A⁶, and A⁷ is N and the others are —C(R$_F$)—, A⁸, A⁹, and A¹⁰ are —C(R$_F$)—, or one or two of A⁸, A⁹, and A¹⁰ is N and the others are —C(R$_F$)—, wherein R$_E$ and R$_F$, at each occurrence, are each independently selected from the group consisting of hydrogen, alkyl, alkenyl, CN, NO₂, halogen, hydroxy, alkoxy, —NH₂, —N(H)alkyl, —N(alkyl)₂, —SH, —S(alkyl), —S(O)₂alkyl, —S(O)₂Oalkyl, —C(O)OH, —C(O)Oalkyl, —C(O)H, haloalkyl, cyanoalkyl, nitroalkyl, hydroxyalkyl, alkoxyalkyl and haloalkoxyalkyl. Particularly, A¹, A², A³, A⁴ are —C(R$_E$)—, or one of A¹, A², A³, A⁴ is N and the others are —C(R$_E$)—, A⁵, A⁶, and A⁷ are —C(R$_F$)—, or one of A⁵, A⁶, and A⁷ is N and the others are —C(R$_F$)—, A⁸, A⁹, and A¹⁰ are —C(R$_F$)—, or one of A⁸, A⁹, and A¹⁰ is N and the others are —C(R$_F$)—, wherein R$_E$ and R$_F$ are as previously described. More particularly, A¹, A², A³, A⁴ are —C(R$_E$)—, or one of A¹, A², A³, A⁴ is N and the others are —C(R$_E$)—, A⁵, A⁶, and A⁷ are or one of A⁵, A⁶, and A⁷ is N and the others are —C(R$_F$)—, A⁸, A⁹, and A¹⁰ are —C(R$_F$)—, or one of A⁸, A⁹, and A¹⁰ is N and the others are —C(R$_F$)—, wherein R$_E$ and R$_F$, at each occurrence, are each independently selected from the group consisting of hydrogen, —I, —Br, —Cl and —F.

It is appreciated that the present invention contemplates compounds of formula (I) with combinations of the above embodiments, including particular, more particular, preferred, more preferred and most preferred embodiments.

Accordingly, one aspect of the invention is related to compounds of formula (I), or a pharmaceutically acceptable salt, prodrug, salt of a prodrug, or a combination thereof, wherein Ar₁ is unsubstituted phenyl or unsubstituted pyridinyl, each of which is fused to an unsubstituted phenyl or unsubstituted pyridinyl; or Ar₁ is a group of formula (a), (b), (c) or (d)

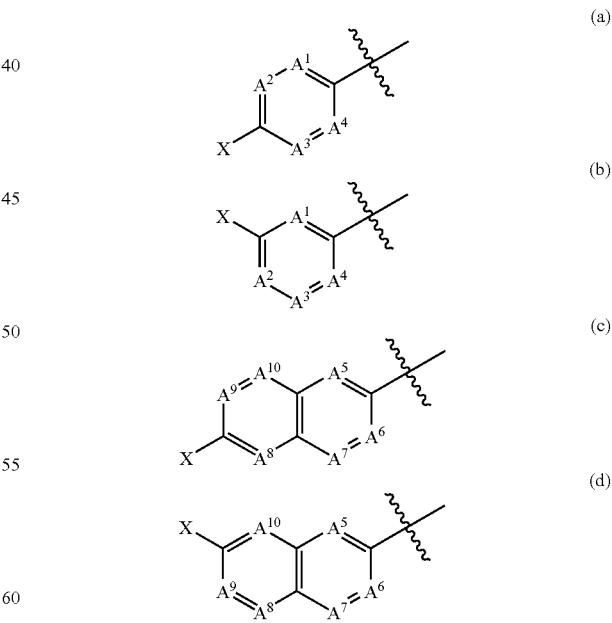

wherein

A¹, A², A³, A⁴ are —C(R$_E$)—, or one or two of A¹, A², A³, A⁴ is N and the others are —C(R$_E$)—, A⁵, A⁶, and A⁷ are —C(R$_F$)—, or one or two of A⁵, A⁶, and A⁷ is N and the others are —C(R$_F$)—, A⁸, A⁹, and A¹⁰ are —C(R$_F$)—, wherein R$_E$ and $R_F$, at each occurrence, are each independently selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; X is —$OR^6$ or —$N(R^7)(R^6)$; wherein $R^6$ and $R^7$ are as described in the summary of the invention; and $L_1$ is —O—. More particularly, $Ar^1$ is unsubstituted phenyl or unsubstituted pyridinyl, each of which is fused to an unsubstituted phenyl or unsubstituted pyridinyl; or $Ar^1$ is a group of formula (a), (b), (c) or (d) wherein $A^1$, $A^2$, $A^3$, $A^4$ are —$C(R_E)$—, or one of $A^1$, $A^2$, $A^3$, $A^4$ is N and the others are —$C(R_E)$—, $A^5$, $A^6$, and $A^7$ are —$C(R_F)$—, or one of $A^5$, $A^6$, and $A^7$ is N and the others are —$C(R_F)$—, $A^8$, $A^9$, and $A^{10}$ are —$C(R_F)$—, or one of $A^8$, $A^9$, and $A^{10}$ is N and the others are —$C(R_F)$—, wherein $R_E$ and $R_F$ are as described above; X is —$OR^6$ wherein $R^6$ is alkyl, aryl or heteroaryl, or X is —$N(R^7)(R^6)$ wherein $R^7$ is hydrogen and $R^6$ is aryl or heteroaryl, wherein each of the aryl and heteroaryl as represented by $R^6$, at each occurrence, are independently unsubstituted or substituted with substituents as described in the summary of the invention; and $L^1$ is —O—. More particularly, $Ar^1$ is unsubstituted phenyl or unsubstituted pyridinyl, each of which is fused to an unsubstituted phenyl or unsubstituted pyridinyl; or $Ar^1$ is a group of formula (a), (b), (c) or (d) wherein $A^1$, $A^2$, $A^3$, $A^4$ are —$C(R_E)$—, or one of $A^1$, $A^2$, $A^3$, $A^4$ is N and the others are —$C(R_E)$—, $A^5$, $A^6$, and $A^7$ are —$C(R_F)$—, or one of $A^5$, $A^6$, and $A^7$ is N and the others are —$C(R_F)$—, $A^8$, $A^9$, and $A^{10}$ are —$C(R_F)$—, or one of $A^8$, $A^9$, and $A^{10}$ is N and the others are —$C(R_F)$—, wherein $R_E$ and $R_F$ are each independently selected from the group consisting of hydrogen, —I, —Br, —Cl and —F; X is —$OR^6$ wherein $R^6$ is $C_1$-$C_6$ alkyl, unsubstituted aryl or aryl substituted with one $C_1$-$C_6$ alkoxy, or X is —$N(R^7)(R^6)$ wherein $R^7$ is hydrogen and $R^6$ is unsubstituted aryl; and $L^1$ is —O—. Preferably, $Ar^1$ is unsubstituted phenyl or unsubstituted pyridinyl, each of which is fused to an unsubstituted phenyl or unsubstituted pyridinyl; or $Ar^1$ is a group of formula (a), (b), (c) or (d) wherein $A^1$, $A^2$, $A^3$, $A^4$ is are —$C(R_E)$—, or one of $A^1$, $A^2$, $A^3$, $A^4$ is N and the others are —$C(R_E)$—, $A^5$, $A^6$, and $A^7$ are —$C(R_F)$—, or one of $A^5$, $A^6$, and $A^7$ is N and the others are —$C(R_F)$—, $A^8$, $A^9$, and $A^{10}$ are —$C(R_F)$—, or one of $A^8$, $A^9$, and $A^{10}$ is N and the others are —$C(R_F)$—, wherein $R_E$ and $R_F$ are each independently selected from the group consisting of hydrogen, —I, —Br, —Cl and —F; X is —$OR^6$ wherein $R^6$ is methyl, isopropyl, phenyl or naphthyl, or X is —$N(R^7)(R^6)$ wherein $R^7$ is hydrogen and $R^6$ is phenyl or naphthyl; wherein the naphthyl and phenyl as represented by $R^6$ are each independently unsubstituted or substituted with one isopropoxy; and $L^1$ is —O—.

Another aspect of the invention relates to compounds of formula (I), or a pharmaceutically acceptable salt, prodrug, salt of a prodrug, or a combination thereof, wherein $Ar^1$ is unsubstituted phenyl or unsubstituted pyridinyl, each of which is fused to an unsubstituted phenyl or unsubstituted pyridinyl; or $Ar^1$ is a group of formula (a), (b), (c) or (d)

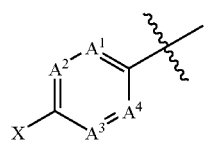

(a)

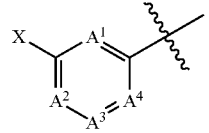

(b)

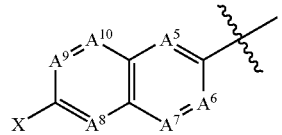

(c)

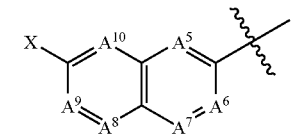

(d)

$A^1$, $A^2$, $A^3$ and $A^4$ are —$C(R_E)$—,
$A^5$, $A^6$, and $A^7$ are —$C(R_F)$—,
$A^8$, $A^9$, and $A^{10}$ are —$C(R_F)$—,
wherein $R_E$ and $R_F$, at each occurrence, are each independently selected from the group consisting of hydrogen, —I, —Br, —Cl, and —F;
$R_A$, $R_B$ and $R_C$ are hydrogen;
$L^1$ is —O—
X is —$OR^6$ wherein $R^6$ is selected from the group consisting of $C_1$-$C_6$ alkyl and aryl, or —$N(R^7)(R^6)$ wherein $R^7$ is hydrogen and $R^6$ is aryl;
$R^1$ is $C_1$-$C_6$ alkyl or $C_1$-$C_6$ haloalkyl; and
Z is —CN, —$OR^2$, —$N(R^3)(R^4)$, or —$C_1$-$C_6$ alkylenyl-$N(R^3)(R^4)$; wherein
$R^2$ is hydrogen or —$C(O)R_a$ wherein $R_a$ is $C_1$-$C_6$ alkyl;
$R^3$ is hydrogen; and
$R^4$ is hydrogen, —$C(O)R_a$ wherein $R_a$ is $C_1$-$C_6$ alkyl, or —$C(O)N(R_a)(R_b)$ wherein $R_a$ is hydrogen and $R_b$ is hydrogen or $C_1$-$C_6$ alkyl.

Another aspect of the invention relates to compounds of formula (I), or a pharmaceutically acceptable salt, prodrug, salt of a prodrug, or a combination thereof, wherein $Ar^1$ is formula (a),

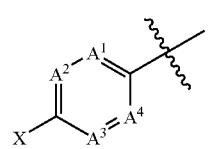

(a)

$A^1$, $A^2$, $A^3$ and $A^4$ are —$C(R_E)$—, or one of $A^1$, $A^2$, $A^3$ and $A^4$ is N and the others are —$C(R_E)$—; wherein $R_E$ is selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;

X is —$OR^6$ wherein $R^6$ is selected from the group consisting of $C_1$-$C_6$ alkyl, unsubstituted aryl and aryl substituted with substituents as described in the summary of the invention;

$L^1$ is —O—;
$R^1$ is $C_1$-$C_6$ alkyl or $C_1$-$C_6$ haloalkyl;

Z is —CN, —OR$^2$, —N(R$^3$)(R$^4$), or —C$_1$-C$_6$ alkylenyl-N(R$^3$)(R$^4$); wherein
  R$^2$ is hydrogen or —C(O)R$_a$ wherein R$_a$, is C$_1$-C$_6$ alkyl;
  R$^3$ is hydrogen; and
  R$^4$ is hydrogen, —C(O)R$_a$ wherein R$_a$, is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$ and R$_C$ are as described in the summary of the invention.

Another aspect of the invention relates to compounds having formula (I), or a pharmaceutically acceptable salt, prodrug, salt of a prodrug, or a combination thereof, wherein Ar$^1$ is formula (a),

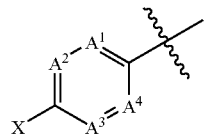

(a)

A$^1$, A$^2$, A$^3$ and A$^4$ are —C(R$_E$)—, or one of A$^1$, A$^2$, A$^3$ and A$^4$ is N and the others are —C(R$_E$)—; wherein each R$_E$ is independently selected from the group consisting of hydrogen, —I, —Br, —Cl, and —F;
  R$_A$, R$_B$ and R$_C$ are hydrogen;
  X is —OR$^6$ wherein R$^6$ is selected from the group consisting of methyl, isopropyl, phenyl, and naphthyl, wherein the phenyl and naphthyl are independently unsubstituted or substituted with one isopropoxy;
  L$^1$ is —O—;
  R$^1$ is methyl; and
  Z is —CN, —OR$^2$, —N(R$^3$)(R$^4$), or —CH$_2$—N(R$^3$)(R$^4$); wherein
    R$^2$ is hydrogen or —C(O)(methyl);
    R$^3$ is hydrogen; and
    R$^4$ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar$^1$ is formula (a),

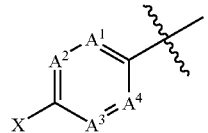

(a)

A$^1$, A$^2$, A$^3$ and A$^4$ are —C(R$_E$)—, or one of A$^1$, A$^2$, A$^3$ and A$^4$ is N and the others are —C(R$_E$)—, wherein R$_E$ is selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;
  X is —N(R$^6$)(R$^7$) wherein R$^7$ is hydrogen and R$^6$ is aryl, unsubstituted or substituted with substituents as described in the summary of the invention;
  L$^1$ is —O—;
  R$^1$ is C$_1$-C$_6$ alkyl or C$_1$-C$_6$ haloalkyl;
  Z is —CN, —OR$^2$, —N(R$^3$)(R$^4$), or —C$_1$-C$_6$ alkylenyl-N(R$^3$)(R$^4$); wherein
    R$^2$ is hydrogen or —C(O)R$_a$ wherein R$_a$, is C$_1$-C$_6$ alkyl;
    R$^3$ is hydrogen; and
    R$^4$ is hydrogen, —C(O)R$_a$ wherein R$_a$ is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$ and R$_C$ are as described in the summary of the invention.

Another aspect of the invention relates to compounds having formula (I), or a pharmaceutically acceptable salt, prodrug, salt of a prodrug, or a combination thereof, wherein Ar$^1$ is formula (a),

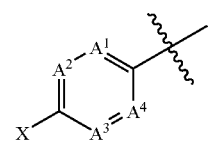

(a)

A$^1$, A$^2$, A$^3$ and A$^4$ are —C(R$_E$)—, or one of A$^1$, A$^2$, A$^3$ and A$^4$ is N and the others are —C(R$_E$)—; wherein each R$_E$ is independently selected from the group consisting of hydrogen, —I, —Br, —Cl, and —F;
  X is —N(R$^6$)(R$^7$) wherein R$^7$ is hydrogen and R$^6$ is phenyl or naphthyl wherein each R$^6$ is independently unsubstituted or substituted with one isopropoxy;
  R$_A$, R$_B$ and R$_C$ are hydrogen;
  L$^1$ is —O—;
  R$^1$ is methyl; and
  Z is —CN, —OR$^2$, —N(R$^3$)(R$^4$), or —CH$_2$—N(R$^3$)(R$^4$); wherein
    R$^2$ is hydrogen or —C(O)(methyl);
    R$^3$ is hydrogen; and
    R$^4$ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar$^1$ is formula (b),

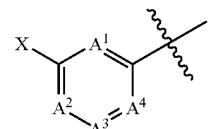

(b)

A$^1$, A$^2$, A$^3$ and A$^4$ are —C(R$_E$)—, or one of A$^1$, A$^2$, A$^3$ and A$^4$ is N and the others are —C(R$_E$)—; wherein R$_E$ is selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;
  X is —OR$^6$ wherein R$^6$ is selected from the group consisting of C$_1$-C$_6$ alkyl, unsubstituted aryl and aryl substituted with substituents as described in the summary of the invention;
  L$^1$ is —O—;
  R$^1$ is C$_1$-C$_6$ alkyl or C$_1$-C$_6$ haloalkyl; and
  Z is —CN, —OR$^2$, —N(R$^3$)(R$^4$), or —C$_1$-C$_6$ alkylenyl-N(R$^3$)(R$^4$); wherein
    R$^2$ is hydrogen or —C(O)R$_a$ wherein R$_a$, is C$_1$-C$_6$ alkyl;
    R$^3$ is hydrogen;

R⁴ is hydrogen, —C(O)R$_a$ wherein R$_a$ is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$, R$_C$ are as described in the summary of the invention.

Another aspect of the invention relates to compounds having formula (I), or a pharmaceutically acceptable salt, prodrug, salt of a prodrug, or a combination thereof, wherein Ar¹ is formula (b),

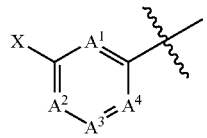

(b)

A¹, A², A³ and A⁴ are —C(R$_E$)—, or one of A¹, A², A³ and A⁴ is N and the others are —C(R$_E$)—; wherein each R$_E$ is independently selected from the group consisting of hydrogen, —I, —Br, —Cl, and —F;

R$_A$, R$_B$ and R$_C$ are hydrogen;

X is —OR⁶ wherein R⁶ is selected from the group consisting of methyl, isopropyl, phenyl and naphthyl, wherein the phenyl and the naphthyl are independently unsubstituted or substituted with one isopropoxy;

L¹ is —O—;

R¹ is methyl; and

Z is —CN, —OR², —N(R³)(R⁴), or —CH$_2$—N(R³)(R⁴); wherein

R² is hydrogen or —C(O)(methyl);

R³ is hydrogen; and

R⁴ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar¹ is formula (b),

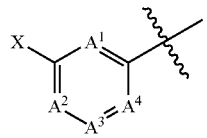

(b)

A¹, A², A³ and A⁴ are —C(R$_E$)—, or one of A¹, A², A³ and A⁴ is N and the others are —C(R$_E$)—; wherein R$_E$ is selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;

X is —N(R⁶)(R⁷) wherein R⁷ is hydrogen and R⁶ is aryl, unsubstituted or substituted with substituents as described in the summary of the invention;

L¹ is —O—;

R¹ is C$_1$-C$_6$ alkyl or C$_1$-C$_6$ haloalkyl;

Z is —CN, —OR², —N(R³)(R⁴), or —C$_1$-C$_6$ alkylenyl-N(R³)(R⁴); wherein

R² is hydrogen or —C(O)R$_a$ wherein R$_a$, is C$_1$-C$_6$ alkyl;

R³ is hydrogen; and

R⁴ is hydrogen, —C(O)R$_a$ wherein R$_a$ is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$, and R$_C$ are as described in the summary of the invention.

Another aspect of the invention relates to compounds having formula (I), or a pharmaceutically acceptable salt, prodrug, salt of a prodrug, or a combination thereof, wherein Ar¹ is formula (b),

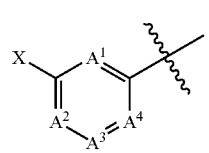

(b)

A¹, A², A³ and A⁴ are —C(R$_E$)—, or one of A¹, A², A³ and A⁴ is N and the others are —C(R$_E$)—; wherein each R$_E$ is independently selected from the group consisting of hydrogen, —I, —Br, —Cl, and —F;

R$_A$, R$_B$ and R$_C$ are hydrogen;

X is —N(R⁶)(R⁷) wherein R⁷ is hydrogen and R⁶ is phenyl or naphthyl, wherein each R⁶ is independently unsubstituted or substituted with one isopropoxy;

L¹ is —O—;

R¹ is methyl; and

Z is —CN, —OR², —N(R³)(R⁴), or —CH$_2$—N(R³)(R⁴); wherein

R² is hydrogen or —C(O)(methyl);

R³ is hydrogen; and

R⁴ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar¹ is formula (c) or (d),

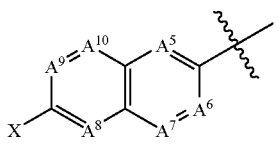

(c)

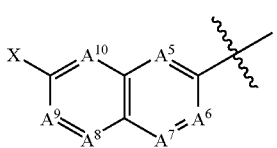

(d)

A⁵, A⁶, and A⁷ are —C(R$_F$)—, or one of A⁵, A⁶, and A⁷ is N and the others are

A⁸, A⁹, and A¹⁰ are —C(R$_F$)—, or one of A⁸, A⁹, and A¹⁰ is N and the others are —C(R$_F$)—;

R$_F$, at each occurrence, is independently selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;

X is OR⁶ wherein R⁶ is C$_1$-C$_6$ alkyl or aryl, or —N(R⁶)(R⁷) wherein R⁷ is hydrogen and R⁶ is aryl, wherein the aryl as represented by R⁶ is unsubstituted or substituted with substituents as described in the summary of the invention;

L¹ is —O—;

R¹ is C$_1$-C$_6$ alkyl or C$_1$-C$_6$ haloalkyl;

Z is —CN, —OR$^2$, —N(R$^3$)(R$^4$), or —C$_1$-C$_6$ alkylenyl-N(R$^3$)(R$^4$); wherein
R$^2$ is hydrogen or —C(O)R$_a$ wherein R$_a$ is C$_1$-C$_6$ alkyl;
R$^3$ is hydrogen; and
R$^4$ is hydrogen, —C(O)R$_a$ wherein R$_a$ is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$ and R$_C$ are as described in the summary of the invention.

Another aspect of the invention relates to compounds having formula (I), or a pharmaceutically acceptable salt, prodrug, salt of a prodrug, or a combination thereof, wherein Ar$^1$ is formula (c) or (d),

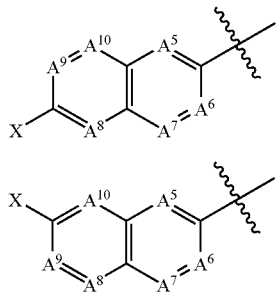

A$^5$, A$^6$, and A$^7$ are —C(R$_F$)—, or one of A$^5$, A$^6$, A$^7$ is N and the others are —C(R$_F$)—,
A$^8$, A$^9$, and A$^{10}$ are —C(R$_F$)—, or one of A$^8$, A$^9$, and A$^{10}$ is N and the others are —C(R$_F$)—,
R$_F$, at each occurrence, are each independently selected from the group consisting of hydrogen, —I, —Br, —Cl and —F;
R$_A$, R$_B$ and R$_C$ are hydrogen;
X is OR$^6$ wherein R$^6$ is selected from the group consisting of methyl, isopropyl, phenyl and naphthyl, wherein the phenyl and naphthyl are independently unsubstituted or substituted with one isopropoxy; or —N(R$^6$)(R$^7$) wherein R$^7$ is hydrogen and R$^6$ is phenyl or naphthyl, wherein the phenyl and naphthyl are independently unsubstituted or substituted with one isopropoxy;
L$^1$ is —O—;
R$^1$ is methyl; and
Z is —CN, —OR$^2$, —N(R$^3$)(R$^4$), or —CH$_2$—N(R$^3$)(R$^4$); wherein
R$^2$ is hydrogen or —C(O)(methyl);
R$^3$ is hydrogen; and
R$^4$ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar$^1$ is unsubstituted phenyl or unsubstituted pyridinyl, each of which is fused to an unsubstituted phenyl or unsubstituted pyridinyl;
L$^1$ is —O—;
R$^1$ is C$_1$-C$_6$ alkyl or C$_1$-C$_6$ haloalkyl; and
Z is —CN, —OR$^2$, —N(R$^3$)(R$^4$), or —C$_1$-C$_6$ alkylenyl-N(R$^3$)(R$^4$); wherein
R$^2$ is hydrogen or —C(O)R$_a$ wherein R$_a$ is C$_1$-C$_6$ alkyl;
R$^3$ is hydrogen; and
R$^4$ is hydrogen, —C(O)R$_a$ wherein R$_a$ is C$_1$-C$_6$ alkyl, or —C(O)N(R$_a$)(R$_b$) wherein R$_a$ is hydrogen and R$_b$ is hydrogen or C$_1$-C$_6$ alkyl; and R$_A$, R$_B$ and R$_C$ are as described in the summary of the invention.

Another aspect of the invention relates to compounds having formula (I), or a pharmaceutically acceptable salt, prodrug, salt of a prodrug, or a combination thereof, wherein Ar$^1$ is unsubstituted phenyl or unsubstituted pyridinyl, each of which is fused to an unsubstituted phenyl or unsubstituted pyridinyl;
L$^1$ is —O—;
R$_A$, R$_B$ and R$_C$ are hydrogen;
R$^1$ is methyl; and
Z is —CN, —OR$^2$, —N(R$^3$)(R$^4$), or —CH$_2$—N(R$^3$)(R$^4$); wherein
R$^2$ is hydrogen or —C(O)(methyl);
R$^3$ is hydrogen; and
R$^4$ is hydrogen, —C(O)(methyl), or —C(O)N(R$_a$)(R$_b$) wherein R$_a$ is hydrogen and R$_b$ is hydrogen or methyl.

Another aspect of the invention relates to compounds having formula (I), or a pharmaceutically acceptable salt, prodrug, salt of a prodrug, or a combination thereof, wherein Ar$^1$ is unsubstituted phenyl or unsubstituted pyridinyl, each of which is fused to an unsubstituted phenyl or unsubstituted pyridinyl; or Ar$^1$ is a group of formula (a), (b), (c) or (d)

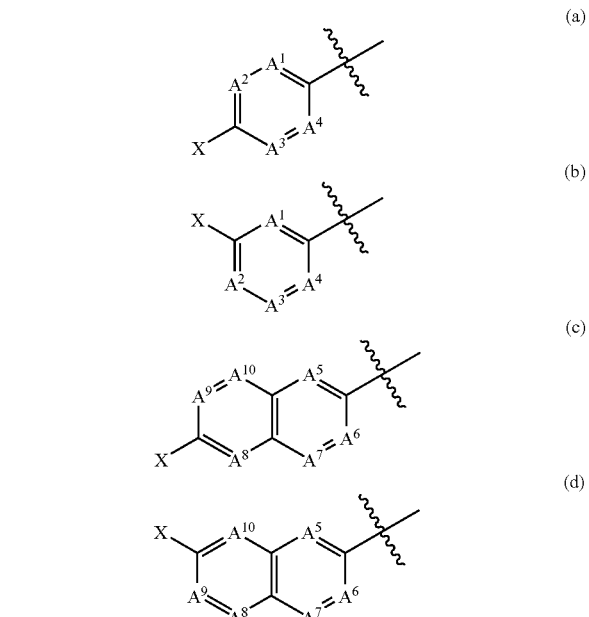

A$^1$, A$^2$, A$^3$ and A$^4$ are —C(R$_E$)—, or one or two of A$^1$, A$^2$, A$^3$ and A$^4$ is N and the others are —C(R$_E$)—,
A$^5$, A$^6$, and A$^7$ are —C(R$_F$)—, or one or two of A$^5$, A$^6$, and A$^7$ is N and the others are —C(R$_F$)—,
A$^8$, A$^9$, and A$^{10}$ are —C(R$_F$)—, or one or two of A$^8$, A$^9$, and A$^{10}$ is N and the others are —C(R$_F$)—,
wherein R$_E$ and R$_F$, at each occurrence, are each independently selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;
X is —OR$^6$ wherein R$^6$ is C$_1$-C$_6$ alkyl, aryl or heteroaryl, or —N(R$^7$)(R$^6$) wherein R$^7$ is hydrogen and R$^6$ is aryl or heteroaryl, and the aryl and heteroaryl as represented by R$^6$ are each independently unsubstituted or substituted with substituents as described in the summary of the invention;

$L^1$ is —N(alkyl)- or —N(H)—;
$R^1$ is $C_1$-$C_6$ alkyl or $C_1$-$C_6$ haloalkyl;
Z is —CN, —$OR^2$, —$N(R^3)(R^4)$ or —$C_1$-$C_6$ alkylenyl-N$(R^3)(R^4)$ wherein
  $R^2$ is hydrogen or —C(O)$R_a$ wherein $R_a$ is $C_1$-$C_6$ alkyl;
  $R^3$ is hydrogen; and
  $R^4$ is hydrogen, —C(O)$R_a$ wherein $R_a$ is $C_1$-$C_6$ alkyl, or —C(O)N($R_a$)($R_b$) wherein $R_a$ is hydrogen and $R_b$ is hydrogen or $C_1$-$C_6$ alkyl; and $R_A$, $R_B$ and $R_C$ are as described in the summary of the invention.

Another aspect of the invention relates to compounds having formula (I), or a pharmaceutically acceptable salt, prodrug, salt of a prodrug, or a combination thereof, wherein
$Ar^1$ is unsubstituted phenyl or unsubstituted pyridinyl, each of which is fused to an unsubstituted phenyl or unsubstituted pyridinyl; or $Ar^1$ is a group of formula (a), (b), (c) or (d)

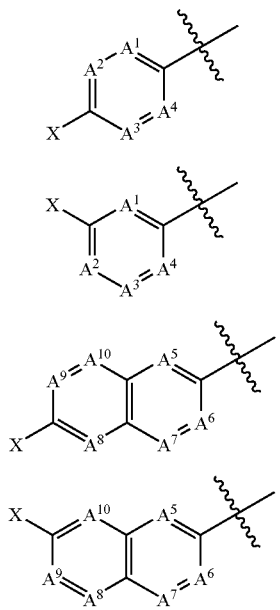

$A^1$, $A^2$, $A^3$ and $A^4$ are —C($R_E$)—, or one or two of $A^1$, $A^2$, $A^3$ and $A^4$ is N and the others are —C($R_E$)—, $A^5$, $A^6$, and $A^7$ are —C($R_F$)—, or one or two of $A^5$, $A^6$, and $A^7$ is N and the others are —C($R_F$)—, $A^8$, $A^9$, and $A^{10}$ are —C($R_F$)—, or one or two of $A^8$, $A^9$, and $A^{10}$ is N and the others are —C($R_F$)—, wherein $R_E$ and $R_F$, at each occurrence, are each independently selected from the group consisting of hydrogen, —I, —Br, —Cl and —F;

X is —$OR^6$ wherein $R^6$ is methyl, isopropyl, phenyl or naphthyl, or —$N(R^7)(R^6)$ wherein
  $R^7$ is hydrogen and $R^6$ is phenyl or naphthyl, and the phenyl and naphthyl as represented by $R^6$ are each independently unsubstituted or substituted with one isopropoxy;

$L^1$ is —N(alkyl)- or —N(H)—;
$R^1$ is methyl;
Z is —CN, —$OR^2$, —$N(R^3)(R^4)$ or —$CH_2$—$N(R^3)(R^4)$ wherein
  $R^2$ is hydrogen or —C(O)(methyl);
  $R^3$ is hydrogen; and
  $R^4$ is hydrogen, —C(O)(methyl), or —C(O)N($R_a$)($R_b$) wherein $R_a$ is hydrogen and $R_b$ is hydrogen or methyl; and
  $R_A$, $R_B$ and $R_C$ are hydrogen.

Exemplary compounds of the present invention having formula (I) include, but are not limited to,
1-[2-(4-phenoxyphenoxy)-1,3-benzothiazol-6-yl]ethanol;
N-{1-[2-(4-phenoxyphenoxy)-1,3-benzothiazol-6-yl]ethyl}acetamide
1-[2-(4-phenoxyphenoxy)-1,3-benzothiazol-6-yl]ethyl acetate;
1-[2-(4-phenoxyphenoxy)-1,3-benzothiazol-6-yl]ethanamine;
2-[2-(4-phenoxyphenoxy)-1,3-benzothiazol-6-yl]propanenitrile;
2-[2-(4-phenoxyphenoxy)-1,3-benzothiazol-6-yl]propan-1-amine;
N-{1-[2-(4-phenoxyphenoxy)-1,3-benzothiazol-6-yl]ethyl}urea;
N-{2-[2-(4-phenoxyphenoxy)-1,3-benzothiazol-6-yl]propyl}acetamide;
2-[2-(4-isopropoxyphenoxy)-1,3-benzothiazol-6-yl]propanenitrile;
2-[2-(4-isopropoxyphenoxy)-1,3-benzothiazol-6-yl]propan-1-amine;
N-{2-[2-(4-isopropoxyphenoxy)-1,3-benzothiazol-6-yl]propyl}acetamide;
N-{2-[2-(2-naphthyloxy)-1,3-benzothiazol-6-yl]propyl}acetamide;
N-{2-[2-(3-phenoxyphenoxy)-1,3-benzothiazol-6-yl]propyl}acetamide;
N-{2-[2-(3-isopropoxyphenoxy)-1,3-benzothiazol-6-yl]propyl}acetamide;
N-{2-[2-(4-anilinophenoxy)-1,3-benzothiazol-6-yl]propyl}acetamide;
N-(2-{2-[4-(2-naphthylamino)phenoxy]-1,3-benzothiazol-6-yl}propyl)acetamide;
N-(2-{2-[(6-methoxy-2-naphthyl)oxy]-1,3-benzothiazol-6-yl}propyl)acetamide;
N-(2-{2-[(7-methoxy-2-naphthyl)oxy]-1,3-benzothiazol-6-yl}propyl)acetamide;
N-{2-[2-(quinolin-3-yloxy)-1,3-benzothiazol-6-yl]propyl}acetamide;
N-(2-{2-[4-(4-isopropoxyphenoxy)phenoxy]-1,3-benzothiazol-6-yl}propyl)acetamide;
N-{2-[2-(3-anilinophenoxy)-1,3-benzothiazol-6-yl]propyl}acetamide; and
N-{2-[2-(quinolin-6-yloxy)-1,3-benzothiazol-6-yl]propyl}acetamide;
or a pharmaceutically acceptable salt, prodrug, salt of a prodrug, or a combination thereof.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

The invention also provides pharmaceutical compositions including a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "therapeutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof, oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of ACC by the compounds of the present invention can be delayed by using a liquid suspension of crystalline or amorphous material with poor water solubility. The rate of absorption of the compounds depends upon their rate of dissolution that, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution-retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be microencapsulated with one or more of the excipients discussed previously. The solid dosage forms of tablets, dragees, capsules, pills, and granules can be prepared with coatings and shells such as enteric and release controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Pharmaceutically acceptable salts are well known in the art. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I).

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

The present invention is also directed to a method of inhibiting acetyl-CoA carboxylase (ACC). By inhibiting ACC, the compounds of the present invention can be useful as therapeutic agents for the treatment or prevention of disorders such as but not limited to metabolic syndrome, type TI diabetes, obesity, atherosclerosis and cardiovascular disease. Therefore, according to an embodiment of the present invention compounds of formula (I), can be useful for the treatment of metabolic syndrome, type II diabetes, obesity, atherosclerosis and cardiovascular disease.

Compounds and compositions of the invention are useful for inhibiting the effects of ACC, and more particularly that of ACC1 and ACC2. In particular, the compounds and compositions of the invention can be used for treating and preventing disorders modulated by ACC. Typically, such disorders can be ameliorated by selectively inhibiting the ACC in a mammal, preferably by administering a compound or composition of the invention, either alone or in combination with another active agent, for example, as part of a therapeutic regimen. The compounds of the invention, including but not limited to those specified in the examples, inhibit ACC. As inhibitors of ACC, the compounds of the invention can be useful for the treatment and prevention of a number of ACC mediated diseases or conditions. Compounds of the invention are particularly useful for the treatment or prevention of metabolic syndrome, type TI diabetes, obesity, atherosclerosis and cardiovascular diseases in humans.

Accordingly, the present invention is directed to a method of inhibiting ACC, including administering a therapeutically effective amount of a compound of formula (T).

The present invention is also directed toward a method of inhibiting ACC-1, including administering a therapeutically effective amount of a compound of formula (T).

The present invention is also directed toward a method of inhibiting ACC-2, including administering a therapeutically effective amount of a compound of formula (T).

Another embodiment of the present invention is directed toward a method of treating metabolic syndrome in a mammal, including administering a therapeutically effective amount of a compound of formula (T).

Another embodiment of the present invention is directed toward a method of treating type TI diabetes in a mammal, including administering a therapeutically effective amount of a compound of formula (I).

Another embodiment of the present invention is directed toward a method of treating obesity, including administering a therapeutically effective amount of a compound of formula (I).

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) to effectively ameliorate disorders by inhibiting ACC at a reasonable benefit/risk ratio applicable to any medical treatment. The specific therapeutically effective dose level for any particular patient depends upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of ACC in single or divided doses can be in amounts, for example, from about 0.1 to 50 mg/kg body weight. In a more preferred range, compounds of the present invention inhibit the action of ACC in a single or divided doses from about 1 to 25 mg/kg body weight. Single dose compositions can contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

Biological Data

The ACC2 enzymatic assay has been developed using either crude digitonin lysates of hACC2 overexpressing HEK 293 cells or recombinant human ACC2 expressed in baculovirus/Sf9 system. In both cases in order to increase the expression and solubility of the protein, a chimeric version of ACC2 ("mito-minus"), in which the N-terminal transmembrane domain (1-275 aa's of ACC2) was replaced with the corresponding ACC1 sequence (1-133 aa's). The enzymatic assay measures ACC mediated incorporation of [$^{14}$C] $CO_2$ into [$^{14}$C]-Malonyl CoA. Mono-Avidin purified rat liver ACC1 was used as ACC1 enzyme source for the ACC-1 activity assay. The assay was preformed in 40 μL reaction in a 96-well plate format. The 1× assay buffer contains 50 mM Hepes/NaOH, pH 7.5, 10 mM citrate, 20 mM $MgCl_2$ and 0.075% BSA. First, 20 μL of test compounds was dissolved in 1% DMSO in 1× assay buffer was dispensed into 96-well. Then, 10 μL of enzyme in 1× assay buffer was dispensed. The reaction was initiated by adding the following substrate mixture in 1× assay buffer: 2 mM ATP, 1 mM acetyl-CoA, and 17.6 mM $NaHCO_3$ (0.12 μCi). The reaction was carried out at room temperature for 40 minutes and the reaction was terminated by adding 50 μL of 1N HCl. The plate was air-dried in a fume hood at room temperature overnight. 20 μL of distilled water was added followed by adding 150 μL of SuperMix liquid scintillation fluid (PerkinElmer). The radioactivity was determined in PerkinElmer microbeta after vigorous shaking. The $IC_{50}$ value was calculated from 8-dose response curve of test compounds.

TABLE 1

| Inhibition of ACC1 and ACC2 Enzymatic Activities | |
|---|---|
| ACC1 IC50 (μM) | ACC2 IC50 (μM) |
| 20 | 4.3 |
| 19 | 3.6 |
| 7 | 3.3 |
| 0.49 | 0.086 |
| 1.6 | 0.27 |
| >30 | 20 |
| 1.4 | 0.14 |
| 0.66 | 0.19 |
| >30 | 6.7 |
| >30 | 11 |
| 0.071 | 0.032 |
| >30 | 4.5 |
| 3.5 | 0.15 |
| 0.036 | 0.09 |
| 0.49 | 0.38 |
| 0.61 | 1.6 |
| >30 | 4.5 |
| 0.68 | 0.97 |
| 17 | >30 |
| 5.6 | >30 |
| >30 | 5.4 |
| >30 | 4.6 |

Dysregulation of fatty acids metabolism contributes to decreased insulin sensitivity and the development of metabolic syndrome. ACC is known to modulate fatty acid synthesis and fatty acid oxidation in insulin responsive tissues such as liver, adipose and skeletal muscles. The ACC inhibitors of the present invention have the potential to decrease de novo lipid synthesis and increase fat oxidation in vivo. Therefore, these chemotypes represent a novel method to treat insulin resistance/type 2 diabetes, as well as obesity, hypertension and hyperlipidemia.

Synthetic Methods

The compounds and processes of the present invention will be better understood in connection with the following synthetic schemes, which together illustrate the methods by which the compounds of the invention can be prepared. The synthesis of compounds of formula (I) wherein the groups $Ar^1$, $R^1$, $R^4$, $L^1$, Z, $R_A$, $R_B$ and $R_C$ are as defined in the summary of the invention unless otherwise noted, are exemplified in Schemes 1-4.

Starting materials can be obtained from commercial sources or prepared by well-established literature methods known to those of ordinary skill in the art.

This invention is intended to encompass compounds having formula (I) when prepared by synthetic processes or by metabolic processes. Preparation of the compounds of the invention by metabolic processes includes those occurring in the human or animal body (in vivo) or processes occurring in vitro.

As used in the descriptions of the schemes and the examples, certain abbreviations are intended to have the following meanings: DMSO for dimethylsulfoxide; and HPLC for high-pressure liquid chromatography.

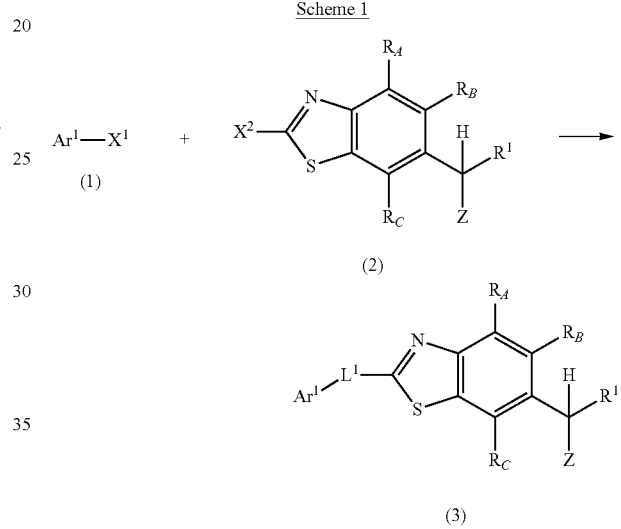

Scheme 1

Compounds of formula (3) wherein $Ar_1$, $R_A$, $R_B$, $R_C$, $R^1$, and Z are as defined in formula (I), and $L^1$ is —O—, —N(alkyl)-, —N(H)— or —S—, can be prepared as shown in Scheme 1.

Compounds of formula (1) wherein $X^1$ is $L^1$-H, can be reacted with compounds of formula (2) wherein $X^2$ is Br, Cl, F or triflate, and $X^3$ is —CN, —O—C(O)$CH_3$, -alkylenyl-OC(O)$CH_3$, —N($R^3$)(P) or -alkylenyl-N($R^3$)(P), wherein P is acetyl, phthalimide, benzyl, benzyloxycarbonyl or tert-butoxycarbonyl, in the presence of a base such as, but not limited to sodium hydride or potassium carbonate, and optionally in the presence of 18-crown-6. The reaction can generally be performed in a solvent such as, but not limited to, N,N-dimethylformamide or dimethylsulfoxide, at a temperature from about room temperature to about 180° C. The reaction can also be conducted in a microwave oven. It is appreciated compounds of formula (3) can also be obtained from the reaction of formula (1) wherein $X^1$ is Br, Cl, F or triflate, and compounds of formula (2) wherein $X^2$ is $L^1$-H.

Alternatively, the transformation can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, sodium tert-butoxide, cesium carbonate, or sodium hydride. The reaction is generally performed at a temperature from about room temperature to about 180° C., in a solvent such as, but not limited to, toluene or N,N-dimethylformamide.

Compounds of formula (1) wherein $X^1$ is $L^1$-H, when reacted with compounds of formula (2) wherein $X^2$ is —Sn(alkyl)$_3$, and Z is —CN, —O—C(O)CH$_3$, -alkylenyl-OC(O)CH$_3$, —N(R$^3$)(P) or -alkylenyl-N(R$^3$)(P), wherein P is acetyl, phthalimide, benzyl, benzyloxycarbonyl or tert-butoxycarbonyl, in the presence of a palladium source such as tris(dibenzylidineacetone)dipalladium, tetrakis(triphenylphosphine) palladium(0), and optionally in the presence of a ligand such as tri(2-furyl)phosphine or triphenylarsine, provide compounds of formula (3). It is appreciated compounds of formula (3) can also be obtained from the reaction of formula (1) wherein $X^1$ is —Sn(alkyl)$_3$, and compounds of formula (2) wherein $X^2$ is $L^1$-H and Z is —CN, —O—C(O)CH$_3$, -alkylenyl-OC(O)CH$_3$, —N(R$^3$)(P) or -alkylenyl-N(R$^3$)(P), wherein P is acetyl, phthalimide, benzyl, benzyloxycarbonyl or tert-butoxycarbonyl, using the aforementioned reaction conditions.

Stannanes of formula (1) when $X^1$ is —Sn(alkyl)$_3$ or (2) when $X^2$ is —Sn(alkyl)$_3$ can be purchased or prepared from heteroarylhalides, heteroaryltriflates, arylhalides or aryltriflates by reaction with hexa-alkyl distannanes of formula ((alkyl)$_3$Sn)$_2$ in the presence of a palladium source like tetrakis(triphenylphosphine) palladium(0). Alternatively, stannanes of formula (1) or (2) can be obtained from metal-halogen exchange of compounds of formula (1) or (2) wherein $X^1$ or $X^2$ is bromide, with n-butyl lithium at about −78° C., followed by reaction with tributyl tin halide at a temperature from about −78° C. to about room temperature, in a solvent such as tetrahydrofuran.

Compounds of formula (3) wherein Z is —N(R$^3$)(P) or -alkylenyl-N(R$^3$)(P), and P is acetyl, phthalimide, benzyl, benzyloxycarbonyl or tert-butoxycarbonyl, can be converted to compounds of formula (3) wherein Z is —N(R$^3$)(H) or -alkylenyl-N(R$^3$)(H), by using reaction conditions that are known by one skilled in the art. Many of these manipulations can be found in "Protective Groups in Organic Synthesis", T. W. Greene and P. G. M. Wuts, 3$^{rd}$ edition, John Wiley & Sons, Inc., 1999. For example, conversion of P is phthalimide to P is H can be effected by reaction with hydrazine, in a solvent such as, but not limited to, dichloromethane, ethanol, or a mixture thereof, at a temperature from about room temperature to about the reflux temperature of the solvent employed. The benzyl and benzyloxycarbonyl protecting groups can be removed using hydrogenation in the presence of a catalyst such as, but not limited to, palladium on carbon. Tert-butoxycarbonyl protecting group can be removed by stirring with an acid such as, but not limited to, trifluoroacetic acid, hydrochloric acid or p-toluene sulfonic acid.

Compounds of formula (3) wherein Z is —N(R$^3$)(H) or -alkylenyl-N(R$^3$)(H), can be further derivatized to the corresponding ureas, carbamates, amides and sulfonamides using reaction conditions that are known to one skilled in the art. For example, reaction of the amines of formula (3) wherein Z is —N(R$^3$)(H) or -alkylenyl-N(R$^3$)(H) with trichloroacetyl isocyanate in a solvent such as dichloromethane and the like, at room temperature, followed by refluxing in methanol in catalytic amount of sodium carbonate and water, affords compounds of formula (3) wherein Z is —N(R$^3$)C(O)NH$_2$ or -alkylenyl-N(R$^3$)C(O)NH$_2$. Ureas of formula (3) wherein Z is —N(R$^3$)C(O)N(H)(R$_a$) or -alkylenyl-N(R$^3$)C(O)N(H)(R$_a$) and R$_a$ is as defined in formula (I), can be prepared by treatment of (3) wherein Z is N(R$^3$)(H) or -alkylenyl-N(R$^3$)(H) with isocyanates of formula R$_a$NCO, in a solvent such as dichloromethane and the like, at about room temperature.

Reaction of the amines of formula (3) wherein Z is —N(R$^3$)(H) or -alkylenyl-N(R$^3$)(H) with chloroformates of formula ClC(O)OR$_a$ at room temperature in the presence of an organic base such as, but not limited to, triethylamine or diisopropyl ethyl amine, and in a solvent such as, but not limited to, dichloromethane, affords carbamates of formula (3) wherein Z is —N(R$^3$)C(O)OR$_a$ or -alkylenyl-N(R$^3$)C(O)OR$_a$, and R$_a$ is as defined in formula (I).

The amines of formula (3) wherein Z is —N(R$^3$)(H) or -alkylenyl-N(R$^3$)(H) can also be derivatized by acylating the amines with acetic anhydride or acyl halides of formula R$_a$C(O)Y wherein Y is Br or Cl; and R$_a$ is as defined in formula (I), in the presence of an organic base such as, but not limited to, triethylamine or diisopropyl ethyl amine. The reaction is generally performed in a solvent such as, but not limited to, dichloromethane or tetrahydrofuran, at about room temperature.

Sulfonamides of formula (3) wherein Z is —N(R$^3$)S(O)$_2$R$_a$ or -alkylenyl-N(R$^3$)S(O)$_2$R$_a$, can be prepared from amines of formula (3) wherein Z is —N(R$^3$)(H) or -alkylenyl-N(R$^3$)(H) by treatment with sulfonyl chlorides of formula R$_a$SO$_2$Cl in the presence of an organic base such as, but not limited to, triethylamine or diisopropyl ethyl amine.

Scheme 2

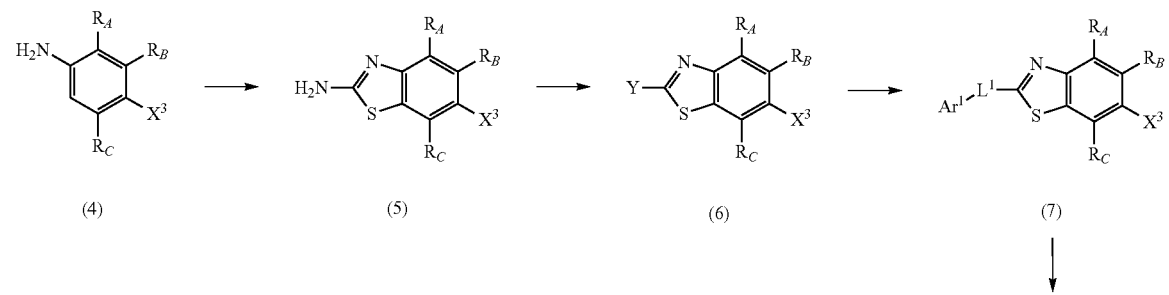

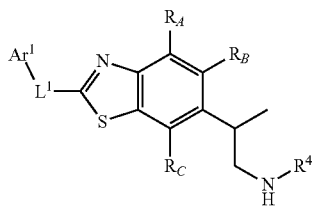 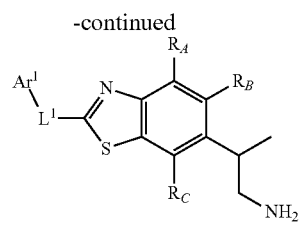 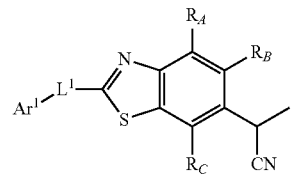

(10) (9) (8)

Compounds of formula (8) and (10) wherein $L^1$-O—, —N(alkyl)-, —N(H) or —S—, $R^4$ is $C(O)OR_a$, —C(O)N$(R_a)(R_b)$, —C(O)R$_a$, or —S(O)$_2$R$_a$ and $R_A$, $R_B$, $R_C$, $R_a$, $R_b$ and Ar$_1$ are as defined in formula (I) can be prepared as outlined in Scheme 2.

Compounds of formula (4) wherein $X^3$ is hydrogen, formyl, $R^1$—C(O)—, —C(H)(R$^1$)(OP$^1$), —C(H)(R$^1$)(-alkylenyl-OP$^1$), —C(H)(R$^1$)(N(R$^3$)(P)), or —C(H)(R$^1$)(-alkylenyl-N(R$^3$)(P)), wherein R$^1$ and R$^3$ are as defined in formula (I), P$^1$ is an oxygen protecting group such as, but not limited to, —Si(alkyl)$_3$, acetyl, or benzyl, and P is a nitrogen protecting group such as, but not limited to, acetyl, phthalimide, benzyl, benzyloxycarbonyl or tert-butoxycarbonyl, together with potassium thiocyanate in acetic acid, can be treated with a solution of bromine in acetic acid at about room temperature, to provide compounds of formula (5).

Bromination of compounds of formula (5) can be achieved by treatment with t-butylnitrite and copper bromide in a solvent such as, but not limited to, acetonitrile, and at about room temperature, to produce compounds of formula (6) wherein Y is Br. The corresponding chloride could also be prepared by substituting copper chloride for copper bromide.

Reaction of compounds of formula (6) wherein Y is Br or Cl, with Ar$^1$-L$^1$-H, using reaction conditions for the transformation of compounds of formula (2) wherein $X^2$ is Br or Cl, to compounds of formula (3) as described in Scheme 1, provides compounds of formula (7).

Compounds of formula (7) wherein $X^3$ is R$^1$—C(O)— and R$^1$ is CH$_3$, when treated with tosylmethyl isocyanate, in the presence of a base such as potassium t-butoxide at about room temperature, provide nitriles of formula (8).

Reduction of the nitriles of formula (8) with hydrogen in the presence of a catalyst such as Raney-Nickel provides amines of formula (9). The reaction is generally conducted in a solvent such as methanol, and at about room temperature. Alternatively, the hydrogenation can be conducted in a mixture of ammonia and methanol in the presence of Raney-Nickel, under about 60 psi of hydrogen and at about room temperature.

Derivatization of amines of formula (9) to amines of formula (10) wherein R$^4$ is —C(O)N(R$_a$)(R$_b$), —C(O)R$_a$, —C(O)OR$_a$ or —S(O)$_2$R$_a$ wherein R$_a$ is as defined in formula (I) is described in Scheme 1.

Scheme 3

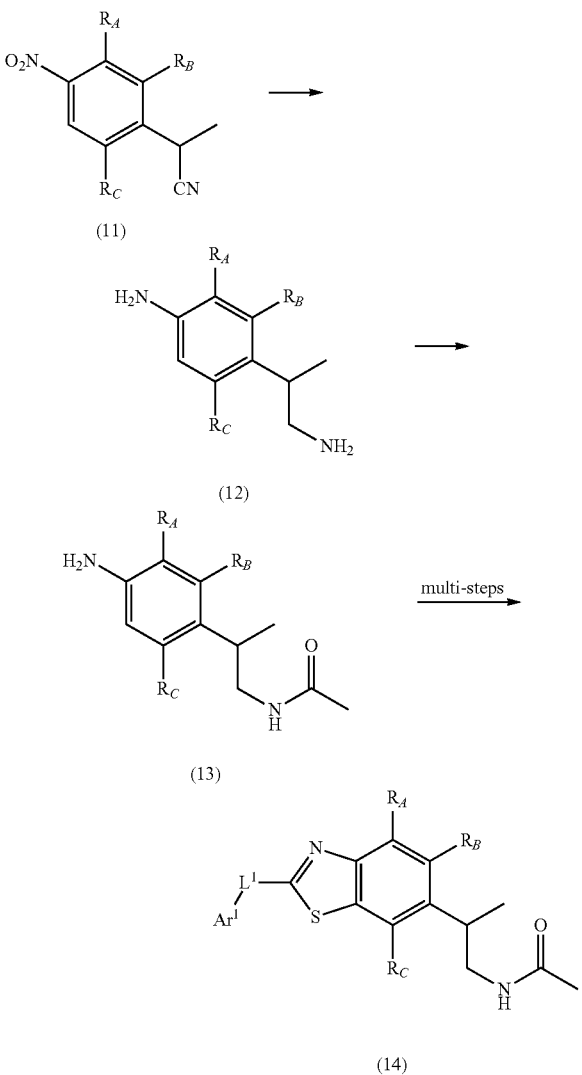

Compounds of formula (14) wherein $L^1$ is —O—, —N(alkyl)-, —N(H)— or —S—, and $R_A$, $R_B$, $R_C$, Ar$^1$ are as defined in formula (I), can be prepared from nitriles of formula (11) as shown in Scheme 3.

Nitriles of formula (11), upon treatment with about 60 psi of hydrogen, in the presence of a catalyst such as, but not limited to, Raney-Nickel, and in a solvent such as, methanol and aqueous ammonia, affords amines of formula (12). Selective acylation of the amines of formula (12) by treatment with about one equivalent of N-acetyl-N-(2-trifluoromethyl-phenyl)acetamide, in a solvent such as, but not limited to, ethanol, and at a temperature of about 0° C. to about room temperature, provides mono acylated amines of formula (13). Using reaction conditions for the transformation of (4) to (7) as described in Scheme 2, amines of formula (13) can be converted to compounds of formula (14).

ethanol, or a mixture thereof, at a temperature from about room temperature to about the reflux temperature of the solvent employed, provides primary amines of formula (18).

Alternatively, compounds of formula (16) can be (a) treated with diphenylphosphorylazide and 1,8-diazabicyclo[5.4.0]undec-7-ene in a solvent such as, but not limited to Scheme 4

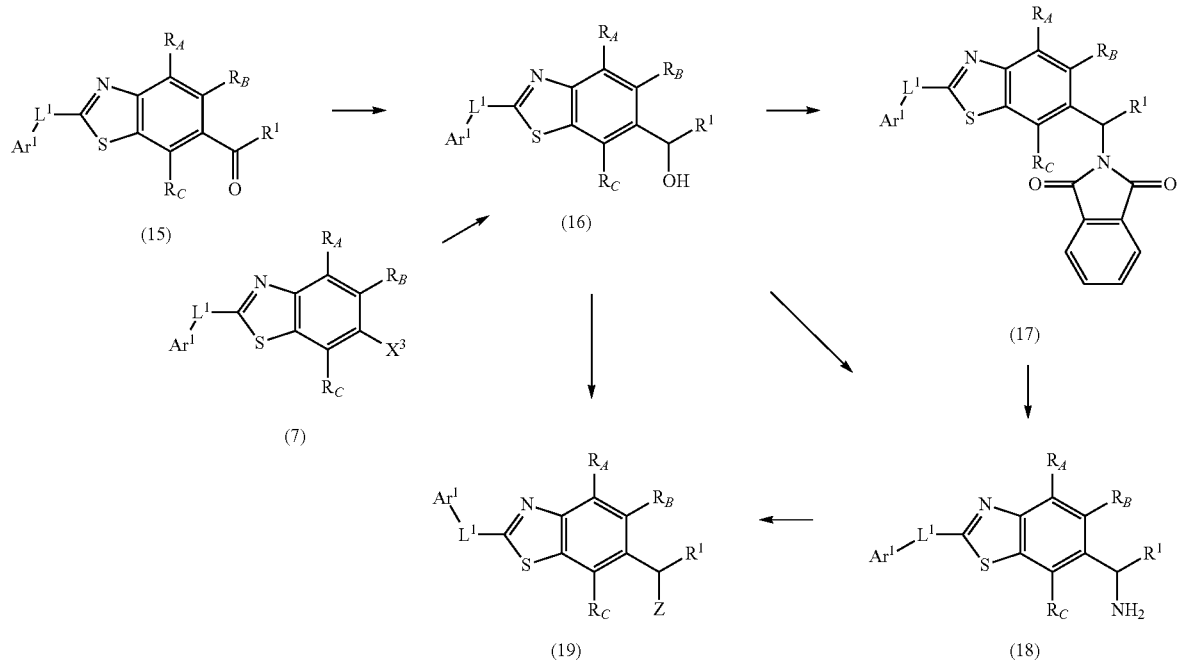

Compounds of formula (19) wherein $L^1$ is —O—, —N(alkyl)-, —N(H)— or —S—, Z is —OR$^2$ or —N(H)(R$^4$), and $R_A$, $R_B$, $R_C$, Ar$^1$, R$^1$, R$^2$ and R$^4$ are as defined in formula (I) can be prepared from compounds of formula (15) or compounds of formula (7) wherein X$^3$ is formyl, as shown in Scheme 4.

Conversion of compounds of formula (7) wherein X$^3$ is hydrogen to compounds of formula (7) wherein X$^3$ is formyl group can be effected by employing n-butyl lithium followed by treatment with a formylation agent such as, but not limited to, N-formylmorpholine.

Compounds of formula (7) wherein X$^3$ is hydrogen can be converted to compounds of formula (16) by treatment with a lithium base such as, but not limited to, n-butyl lithium in a solvent such as, but not limited to, tetrahydrofuran or dichloromethane, followed by aldehydes of formula R$^1$CHO.

Treatment of compounds of formula (7) wherein X$^3$ is formyl with trimethyl(trifluoromethyl)silane and tetrabutylammonium fluoride in a solvent such as, but not limited to, tetrahydrofuran, provides compounds of formula (16) wherein R$^1$ is trifluoromethyl.

Reduction of compounds of formula (15) with a reducing agent such as, but not limited to, sodium borohydride in a mixture of solvent of methanol and tetrahydrofuran affords alcohols of formula (16).

Treatment of alcohols of formula (16) with phthalimide, triphenylphosphine, and diethyl azodicarboxylate in a solvent such as, but not limited to, tetrahydrofuran, at room temperature provides compounds of formula (17).

Treatment of compounds of formula (17) with hydrazine, in a solvent such as, but not limited to, dichloromethane, toluene, at a temperature of about 0° C. to about 50° C.; and (b) treated with the asides obtained from step (a) with triphenylphosphine in a mixture of tetrahydrofuran and water and at about the reflux temperature of the solvent, to provide compounds of formula (18).

Derivatization of amines of formula (18) as described in Scheme 1 provide compounds of formula (19) wherein Z is —N(H)(R$^4$) wherein R$^3$ is as defined in formula (1) and R$^4$ is —C(O)R$_a$, —C(O)N(R$_a$)(R$_b$), —C(O)OR$_a$, or —S(O)$_2$R$_a$ wherein R$_a$, and R$_b$ are as defined in formula (I).

Alternatively, compounds of formula (16) can be converted to compounds of formula (18) wherein Z is —N(H)C(O)CH$_3$, by treatment with acetonitrile in the presence of a mixture of glacial acetic acid and sulfuric acid at room temperature.

Conversion of the alcohols of formula (16) to sulfonates of formula (18) wherein Z is —O—S(O)$_2$R$_a$ wherein R$_a$, is as defined in formula (I) can be achieved by treatment with sulfonyl chlorides of formula R$_a$SO$_2$Cl in the presence of an organic base such as, but not limited to, triethylamine, and optionally in the presence of 4-(dimethylamino)pyridine, in a solvent such as, but not limited to, dichloromethane.

The present invention will now be described in connection with certain preferred embodiments which are not intended to limit its scope. On the contrary, the present invention covers all alternatives, modifications, and equivalents as can be included within the scope of the claims. Routine experimentation, including appropriate manipulation of the reaction conditions, solvents and reagents used, and sequence of the synthetic route, protection of any chemical functionality that can not be compatible with the reaction conditions, and deprotection thereafter are included in the scope of the invention. Synthesis of the compounds of formula (I) can be accomplished by methods analogous to those described above and in the following examples. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.60 (developed by Advanced Chemistry Development, Inc., Toronto, ON, Canada) or were given names consistent with ACD nomenclature.

EXAMPLES

Example 1

1-[2-(4-phenoxyphenoxy)-1,3-benzothiazol-6-yl]ethanone

Example 1A 1-(2-amino-benzothiazol-6-yl)-ethanone

4-Aminoacetophenone (3.0 g, 22.19 mmol) and potassium thiocyanate (8.87 g, 88.78 mmol) were dissolved in acetic acid (35 mL) and stirred together until they dissolved (~15-20 min). The solution was then treated with a solution of bromine (1.14 mL, 22.19 mmol) dissolved in acetic acid (15 mL) by slow addition over 20 min. The reaction was then stirred at room temperature for 19 hr and then poured into $H_2O$ (100 mL). The solution was then basified to pH=9-10 with $NH_4OH$. The resulting precipitate was collected by vacuum filtration. The solids were then dissolved in hot ethyl acetate and filtered again. The filtrate was concentrated in vacuo to give 3.35 g (76%) of the title compound. $^1H$ NMR (300 MHz, DMSO-$d_6$) δ ppm 8.32 (d, J=1.47 Hz, 1H) 7.91 (s, 2H) 7.83 (dd, J=8.46, 1.84 Hz, 1H) 7.37 (d, J=8.46 Hz, 1H) 2.55 (s, 3H). MS m/z (DCI) 193.0 (M+H)$^+$.

Example 1B 1-(2-bromo-benzothiazol-6-yl)-ethanone t-Butylnitrite (2.90 mL, 24.4 mmol) and copper bromide (4.19 g, 18.75 mmol) were dissolved in anhydrous acetonitrile (65 mL). The solution was cooled to 0° C. then it was treated with Example 1A (3.12 g, 16.3 mmol) by portion-wise addition over 20 min. The reaction was then stirred at room temperature for 1.5 hr and poured into 1N HCl (100 mL). This was extracted with ethyl acetate (3×100 mL). The extracts were then washed with $H_2O$ (1×100 mL) followed by brine (1×100 mL). The extracts were dried ($Na_2SO_4$), filtered, and the solvent removed in vacuo. The crude product was purified by flash chromatography ($SiO_2$, 100% hexanes to 10% ethyl acetate in hexanes) to afford 1.84 g (44%) of the title compound.

Example 1C

1-[2-(4-phenoxy-phenoxy)-benzothiazol-6-yl]-ethanone

Example 1B (1.84 g, 7.20 mmol) was dissolved in anhydrous dimethyl sulfoxide (12 mL) and treated with 4-phenoxyphenol (1.41 g, 7.56 mmol) followed by potassium carbonate (1.0 g, 7.20 mmol). The solution was then heated to 130° C. for 3 hr. It was then poured into $H_2O$ (100 mL) and extracted with dichloromethane (5×50 mL). The combined extracts were washed with $H_2O$ (5×100 mL) and brine (1×100 mL). They were dried ($Na_2SO_4$), filtered, and the solvent removed in vacuo. The crude product was purified by flash chromatography ($SiO_2$, 10% ethyl acetate in hexanes to 30% ethyl acetate in hexanes) to afford 2.45 g (94%) of the title compound. $^1H$ NMR (300 MHz, CDCl$_3$) δ ppm 8.33 (d, J=1.84 Hz, 1H) 8.00 (dd, J=8.64, 1.65 Hz, 1H) 7.77 (d, J=8.46 Hz, 1H) 7.23-7.48 (m, 3H) 7.02-7.20 (m, 4H) 6.78-6.98 (m, 1H) 2.65 (s, 3H). MS m/z (DCI) 362.1 (M+H)$^+$.

Example 2

1-[2-(4-phenoxyphenoxy)-1,3-benzothiazol-6-yl]ethanol

Example 1C (1.0 g, 2.77 mmoL) was dissolved in a mixture of ethanol and tetrahydrofuran (1.0 mL, 1:1, v/v). This was treated with sodium borohydride (0.011 g, 2.77 mmol) and the reaction was stirred at room temperature for 1.5 hr. The reaction was then poured into 1N HCl (25 mL) and extracted with ethyl acetate (3×25 mL). The combined extracts were washed with $H_2O$ (1×25 mL) and brine (1×25 mL). The organic layer was dried ($Na_2SO_4$), filtered, and the solvent removed in vacuo to give 1.03 g (100%) of the title compound. It was used in the next step without further purification. $^1H$ NMR (300 MHz, CDCl$_3$) δ ppm 7.70 (s, 1H) 7.68 (s, 1H) 7.19-7.42 (m, 6H) 7.13 (t, J=7.35 Hz, 1H) 6.96-7.09 (m, 3H) 4.98 (q, J=6.37 Hz, 1H) 1.52 (d, J=6.25 Hz, 3H). MS m/z (DCI) 364.1 (M+H)$^+$.

Example 3

N-{1-[2-(4-phenoxyphenoxy)-1,3-benzothiazol-6-yl]ethyl}acetamide

Example 2 (0.095 g, 0.262 mmoL) was dissolved in glacial acetic acid (0.27 mL) and cooled to 0° C. It was then treated with acetonitrile (0.107 mL, 0.137 g, 2.62 mmoL) followed by sulfuric acid (0.03 mL). The reaction was then allowed to stir at room temperature for 16 hr. The reaction was poured into sat NaHCO$_3$ (25 mL). This was extracted with ethyl acetate (1×25 mL). The organic layer was then washed with $H_2O$ (1×25 mL) and brine (1×25 mL). The organic layer was dried ($Na_2SO_4$), filtered, and the solvent removed in vacuo. The crude product was purified by flash chromatography ($SiO_2$, ethyl acetate:hexanes (2:8) to ethyl acetate:hexanes (1:1)) to afford 0.038 g (36%) of the title compound. $^1H$ NMR (300 MHz, CDCl$_3$) δ ppm 7.67 (d, J=8.09 Hz, 1H) 7.63 (d, 1H) 7.25-7.42 (m, 6H) 7.13 (t, J=7.35 Hz, 1H) 7.01-7.10 (m, 3H) 6.06 (d, J=6.62 Hz, 1H) 5.11-5.26 (m, 1H) 1.98 (s, 3H) 1.51 (d, J=6.62 Hz, 3H). MS m/z (DCI) 405.1 (M+H)$^+$.

Example 4

1-[2-(4-phenoxyphenoxy)-1,3-benzothiazol-6-yl]ethyl acetate

Example 2 (0.095 g, 0.262 mmoL) was dissolved in glacial acetic acid (0.27 mL) and cooled to 0° C. It was then treated with acetonitrile (0.107 mL, 0.137 g, 2.62 mmoL) followed by sulfuric acid (0.03 mL). The reaction was then allowed to stir at room temperature for 16 hr. The reaction was poured into sat NaHCO$_3$ (25 mL). This was extracted with ethyl acetate (1×25 mL). The organic layer was then washed with H₂O (1×25 mL) and brine (1×25 mL). The organic layer was dried (Na₂SO₄), filtered, and the solvent removed in vacuo. The crude product was purified by flash chromatography (SiO₂, ethyl acetate:hexanes (2:8) to ethyl acetate:hexanes (1:1)) to afford 0.044 g (42%) of the title compound. ¹H NMR (300 MHz, CDCl₃) δ ppm 7.65-7.76 (m, 2H) 7.23-7.44 (m, 5H) 6.98-7.19 (m, 4H) 6.86-6.97 (m, 1H) 6.74-6.83 (m, 1H) 5.95 (q, J=6.62 Hz, 1H) 2.08 (s, 3H) 1.57 (d, J=6.62 Hz, 3H). MS m/z (DCI) 406.1 (M+H)⁺.

Example 5

1-[2-(4-phenoxyphenoxy)-1,3-benzothiazol-6-yl]ethanamine

Example 5A 6-(1-azidoethyl)-2-(4-phenoxyphenoxy)benzo[d]thiazole

Example 2 (0.415 g, 1.14 mmoL) was dissolved in anhydrous toluene (2 mL) and treated with diphenylphosphorylazide (0.30 mL, 0.380 g, 1.38 mmoL). The solution was then cooled to 0° C. and treated with 1,8-diazabicyclo[5.4.0]undec-7-ene (0.207 mL, 0.210 g, 1.38 mmoL). It was stirred at 0° C. for 2 hr then at room temperature for 40 hr then at 45° C. for 3 hr. The reaction was then diluted with ethyl acetate (25 mL) and washed with 1N HCl (1×25 mL), H₂O (1×25 mL), and brine (1×25 mL). The organic layer was dried (Na₂SO₄), filtered, and the solvent removed in vacuo. The crude product was purified by flash chromatography (SiO₂, ethyl acetate:hexanes (3:97) to ethyl acetate:hexanes (1:9)) to afford 0.267 g (60%) of the title compound. ¹H NMR (300 MHz, CDCl₃) δ ppm 7.95 (d, 1H) 7.7 (d, J=8.09 Hz, 1H) 7.38-7.45 (m, 5H) 7.05-7.20 (m, 5H) 4.90 (q, J=6.62 Hz, 1H) 1.45 (d, J=6.62 Hz, 3H). MS m/z (DCI) 389.1 (M+H)⁺.

Example 5B 1-(2-(4-phenoxyphenoxy)benzo[d]thiazol-6-yl)ethanamine

Example 5A (0.132 g, 0.358 mmoL) was dissolved in a mixture of tetrahydrofuran (3.0 mL)/H₂O (0.02 mL). This was then treated with triphenylphosphine (0.137 g, 0.510 mmoL) and heated to reflux for 16 hr. The reaction was diluted with ethyl acetate (25 mL) and washed with brine (1×25 mL). The organic layer was dried (Na₂SO₄), filtered, and the solvent removed in vacuo. The crude product was purified by flash chromatography (SiO₂, 100% dichloromethane to 96 dichloromethane+2% NH₄OH/4 methanol+2% NH₄OH) to afford 0.078 g (60%) of the title compound. ¹H NMR (300 MHz, CDCl₃) δ ppm 7.70 (s, 2H) 7.68 (s, 1H) 7.24-7.42 (m, 5H) 7.02-7.19 (m, 6H) 4.23 (q, J=6.37 Hz, 1H) 1.43 (d, J=6.62 Hz, 3H). MS m/z (DCI) 363.1 (M+H)⁺.

Example 6

2-[2-(4-phenoxyphenoxy)-1,3-benzothiazol-6-yl]propanenitrile

Example 1C (0.250 g, 0.693 mmoL) was dissolved in anhydrous DME (3.0 mL) and treated with tosylmethyl isocyanate (0.284 g, 1.45 mmoL). The solution was then cooled to 0° C. and treated with a solution of potassium t-butoxide (0.204 g, 1.82 mmoL) dissolved in anhydrous t-butanol (3.0 mL). The reaction was stirred at 0° C. for 15 min then at room temperature for 20 hr. The reaction was then diluted with ethyl acetate (25 mL) and washed with 4% acetic acid (2×25 mL), H₂O (1×25 mL), sat NaHCO₃ (1×25 mL), and brine (1×25 mL). The organic layer was dried (Na₂SO₄), filtered, and the solvent removed in vacuo. The crude product was purified by flash chromatography (SiO₂, ethyl acetate:hexanes (15:85) to ethyl acetate:hexanes (35:65)) to afford 0.158 g (61%) of the title compound. ¹H NMR (300 MHz, CDCl₃) δ ppm 7.67-7.82 (m, 1H) 7.23-7.48 (m, 4H) 7.00-7.21 (m, 3H) 6.75-6.99 (m, 1H) 4.12 (q, J=6.99 Hz, 1H) 1.69 (d, J=6.99 Hz, 3H). MS m/z (DCI) 373.1 (M+H)⁺.

Example 7

2-[2-(4-phenoxyphenoxy)-1,3-benzothiazol-6-yl]propan-1-amine

Example 6 (0.051 g, 0.138 mmol) was dissolved in a methanol/2N NH₃ solution. This was treated with Raney-Nickel (0.256 g) and hydrogenated under balloon pressure hydrogen for 2 hr. The reaction was filtered through a pad of Celite and the filtrate concentrated in vacuo. The crude product was purified by flash chromatography (SiO₂, 100% dichloromethane+2% NH₄OH to 94 dichloromethane+2% NH₄OH/6 methanol+2% NH₄OH) to afford 0.027 g (53%) of the title compound. ¹H NMR (300 MHz, CDCl₃) δ ppm 7.69 (d, J=8.46 Hz, 1H) 7.52 (d, J=1.84 Hz, 1H) 7.20-7.45 (m, 4H) 6.99-7.20 (m, 4H) 2.75-2.98 (m, 3H) 1.42 (s, 3H) 1.28 (t, J=6.99 Hz, 3H). MS m/z (DCI) 377.1 (M+H)⁺.

Example 8

N-{1-[2-(4-phenoxyphenoxy)-1,3-benzothiazol-6-yl]ethyl}urea

Example 5B (0.078 g, 0.216 mmoL) was dissolved in anhydrous dichloromethane (3.2 mL) and treated with trichloromethyl isocyanate (0.027 mL, 0.042 g, 0.259 mmoL). The reaction was then stirred at room temperature for 15 min and diluted with dichloromethane (25 mL). It was washed with sat NaHCO₃ (1×25 mL) and brine (1×25 mL). The organic layer was dried (Na₂SO₄), filtered, and the solvent removed in vacuo. The residue was then dissolved in methanol (5 mL) and the solution heated at reflux for 2 hr. After precipitation with diethyl ether 0.027 g (31%) of the title compound was obtained. ¹H NMR (300 MHz, DMSO-d₆) δ ppm 7.82 (d, J=1.84 Hz, 1H) 7.64 (d, J=8.46 Hz, 1H) 7.31-7.52 (m, 5H) 7.05-7.24 (m, 5H) 6.47 (d, J=8.09 Hz, 1H) 5.43 (s, 2H) 4.70-4.86 (m, 1H) 1.34 (d, J=6.99 Hz, 3H). MS m/z (DCI) 406.1 (M+H)⁺.

Example 9

N-{2-[2-(4-phenoxyphenoxy)-1,3-benzothiazol-6-yl]propyl}acetamide

Example 7 (0.020 g, 0.052 mmol) was dissolved in anhydrous dichloromethane (1.0 mL) and cooled to 0° C. It was then treated with triethylamine (0.008 mL, 0.057 mmol) followed by acetyl chloride (0.004 mL, 0.057 mmol). The reaction was then stirred at 0° C. for 1 hr and concentrated in vacuo. The crude product was purified by flash chromatography (SiO₂, ethyl acetate:hexanes (2:8) to 100% ethyl acetate) to afford 0.0072 g (33%) of the title compound. ¹H NMR (300 MHz, CDCl₃) δ ppm 7.69 (d, 1H) 7.52 (d, 1H) 7.20-7.43 (m, 4H) 7.01-7.19 (m, 3H) 5.25-5.38 (m, 1H) 3.59-3.72 (m, 1H) 3.18-3.32 (m, 1H) 2.96-3.13 (m, 1H) 1.56-1.70 (m, 1H) 1.31 (d, 3H) 1.23-1.28 (m, 1H).

Example 10

1-[2-(4-isopropoxyphenoxy)-1,3-benzothiazol-6-yl] ethanone

Example 10A 4-isopropoxyphenol

To a solution of hydroquinone (55.7 g, 0.5 mol) and 2-iodopropane (57.5 g, 0.33 mol) in ethanol was added a solution of potassium hydroxide (78.5 g, 0.5 mol) in water (100 mL). The dark brown solution was then refluxed for 16 hours. Ethanol was removed and the aqueous phase was acidified with 2N HCl and extracted with ethyl acetate (3×200 mL). The combined organic layers were washed with brine, dried (MgSO$_4$) and filtered. The filtrate was concentrated in vacuo to give over 70 g of crude material, which was triturated with dichloromethane and filtered. The filtrate was concentrated and purified on silica gel (5~35% ethyl acetate/hexane) to give 23.0 g of product as a brown oil (46% yield). $^1$H NMR (300 MHz, CDCl$_3$) δ ppm 1.30 (d, J=5.88 Hz, 6H) 4.30-4.50 (m, 1H) 4.78 (s, 1H) 6.66-6.86 (m, 4H). MS (ESI): m/z 151 (M–H). $^1$H NMR (300 MHz, CDCl$_3$) δ ppm 8.31 (d, J=1.84 Hz, 1H) 7.99 (dd, J=8.46, 1.84 Hz, 1H) 7.77 (d, J=9.19 Hz, 1H) 7.20-7.34 (m, 2H) 6.89-7.01 (m, 2H) 4.48-4.62 (m, 1H) 2.65 (s, 3H) 1.37 (d, J=5.88 Hz, 6H). MS m/z (DCI) 405.1 (M+H)$^+$.

Example 10B 1-(2-(4-isopropoxyphenoxy)benzo[d]thiazol-6-yl) ethanone

The reaction was carried out using the same method as described in Example 1C except for substituting Example 10A for Example 1B. The crude product was purified by flash chromatography (SiO$_2$, ethyl acetate:hexanes (1:9) to ethyl acetate:hexanes (3:7)) to afford 0.600 g (85%) of the title compound. $^1$H NMR (300 MHz, CDCl$_3$) δ ppm 8.31 (d, J=1.84 Hz, 1H) 7.99 (dd, J=8.46, 1.84 Hz, 1H) 7.77 (d, J=9.19 Hz, 1H) 7.20-7.34 (m, 2H) 6.89-7.01 (m, 2H) 4.48-4.62 (m, 1H) 2.65 (s, 3H) 1.37 (d, J=5.88 Hz, 6H). MS m/z (DCI) 405.1 (M+H)$^+$.

Example 11

2-[2-(4-isopropoxyphenoxy)-1,3-benzothiazol-6-yl] propanenitrile

The reaction was carried out using the same method as described in Example 6 except for substituting Example 10B for Example 1C. The crude product was purified by flash chromatography (SiO$_2$, ethyl acetate:hexanes (15:85) to ethyl acetate:hexanes (35:65)) to afford 0.303 g (59%) of the title compound. $^1$H NMR (300 MHz, CHLOROFORM-D) δ ppm 7.73 (d, J=8.46 Hz, 1H) 7.68 (d, J=1.84 Hz, 1H) 7.34 (dd, J=8.46, 2.21 Hz, 1H) 7.25 (d, 1H) 7.20-7.29 (m, 2H) 6.94 (d, 1H) 4.48-4.61 (m, 1H) 3.98 (q, J=7.35 Hz, 1H) 1.68 (d, J=7.35 Hz, 3H) 1.36 (d, J=5.88 Hz, 6H). MS m/z (DCI) 339.1 (M+H)$^+$.

Example 12

2-[2-(4-isopropoxyphenoxy)-1,3-benzothiazol-6-yl] propan-1-amine

The reaction was carried out using the same method as described in Example 7 except for substituting Example 11 for Example 6. The crude product was purified by flash chromatography (SiO$_2$, 100 dichloromethane+2% NH$_4$OH to 94 dichloromethane+2% NH$_4$OH/6 methanol+2% NH$_4$OH) to afford 0.148 g (49%) of the title compound. $^1$H NMR (300 MHz, methanol) δ ppm 7.86 (d, J=1.84 Hz, 1H) 7.78 (d, J=8.09 Hz, 1H) 7.49 (dd, J=8.46, 1.84 Hz, 1H) 7.39 (d, 2H) 7.14 (d, 2H) 6.76-6.92 (m, 1H) 4.67-4.82 (m, 1H) 4.45-4.57 (m, 1H) 1.51 (d, J=6.62 Hz, 2H) 1.47 (d, J=5.88 Hz, 6H) 1.37 (d, J=6.25 Hz, 3H). MS m/z (DCI) 343.1 (M+H).

Example 13

N-{2-[2-(4-isopropoxyphenoxy)-1,3-benzothiazol-6-yl]propyl}acetamide

The reaction was carried out using the same method as described in Example 9 except for substituting Example 12 for Example 7. The crude product was purified by flash chromatography (SiO$_2$, ethyl acetate:hexanes (60:40) to 100% ethyl acetate) to afford 0.061 g (47%) of the title compound. $^1$H NMR (300 MHz, DMSO-d$_6$) δ ppm 7.83 (t, J=5.52 Hz, 1H) 7.76 (d, J=1.47 Hz, 1H) 7.60 (d, J=8.46 Hz, 1H) 7.33 (d, 2H) 7.27 (dd, J=8.46, 1.84 Hz, 1H) 7.02 (d, 2H) 4.55-4.70 (m, 1H) 3.14-3.25 (m, 2H) 2.94 (q, J=7.23 Hz, 1H) 1.75 (s, 3H) 1.29 (d, J=6.25 Hz, 6H) 1.16-1.23 (m, 3H). MS m/z (DCI) 385.1 (M+H)$^+$.

Example 14

N-{2-[2-(2-naphthyloxy)-1,3-benzothiazol-6-yl] propyl}acetamide

The reaction was carried out using the same method as described in Example 17E except for substituting 2-hydroxynapthalene for 4-hydroxydiphenylamine. The crude product was purified by flash chromatography (SiO$_2$, 50 ethyl acetate/ 50 hexanes to 100% ethyl acetate) to afford 0.086 g (24%) of the title compound. $^1$H NMR (300 MHz, DMSO-d$_6$) δ ppm 8.09 (d, J=9.19 Hz, 1H) 7.95-8.05 (m, 3H) 7.85 (t, J=5.70 Hz, 1H) 7.81 (d, J=1.47 Hz, 1H) 7.56-7.66 (m, 3H) 7.29 (dd, J=8.27, 1.65 Hz, 1H) 3.21 (t, J=6.43 Hz, 2H) 2.89-3.03 (m, 1H) 1.71-1.80 (m, 3H) 1.20 (d, J=6.43 Hz, 3H). MS m/z (DCI) 377.1 (M+H)$^+$.

Example 15

N-{2-[2-(3-phenoxyphenoxy)-1,3-benzothiazol-6-yl] propyl}acetamide

The reaction was carried out using the same method as described in Example 17E except for substituting 3-phenoxyphenol for 4-hydroxydiphenylamine. The crude product was purified by HPLC using 5-80% acetonitrile and 0.1% trifluoroacetic acid to afford 0.031 g (46%) of the title compound. $^1$H NMR (300 MHz, DMSO-d$_6$) δ ppm 7.84 (t, J=5.70 Hz, 1H) 7.80 (d, J=1.84 Hz, 1H) 7.63 (d, J=8.09 Hz, 1H) 7.39-7.56 (m, 3H) 7.29 (dd, J=8.27, 1.65 Hz, 1H) 7.16-7.24 (m, J=7.35, 7.35 Hz, 2H) 7.06-7.15 (m, 2H) 6.97 (dd, J=8.27, 2.39

Hz, 1H) 3.20 (t, 2H) 2.87-3.02 (m, 1H) 1.71-1.79 (m, 3H) 1.20 (d, J=6.99 Hz, 3H). MS m/z (DCI) 419.1 (M+H)$^+$.

Example 16

N-{2-[2-(3-isopropoxyphenoxy)-1,3-benzothiazol-6-yl]propyl}acetamide

Example 16A 3-isopropoxyphenol

To a mixture of 3-hydroxyphenol (20.0 g, 0.182 mmoL), 2-iodopropane (30.9 g, 0.182 mmoL) in ethanol (25 mL) at refluxing was added KOH (88%, 12.2 g, 0.191 mmoL) in water (30 mL) over a period of 60 min. The resulting mixture was refluxed for 3 hours. The mixture was poured into 1N NaOH and extracted with ether (1×). The aqueous layer was acidified with 10% HCl to pH 5 and extracted with ether (2×). The combined extracts were washed with brine (1×), dried over MgSO$_4$ and concentrated. The residue was purified on silica gel eluting with ethyl acetate:hexane (1:8) to give the desired product as a colorless liquid (11.7 g, 43%). This was used directly in the next step. $^1$H NMR (500 MHz, CDCl$_3$) δ ppm 7.10 (t, 1H) 6.47 (d, J=7.32 Hz, 1H) 6.36-6.42 (m, 1H) 4.70 (s, 1H) 4.45-4.55 (m, 1H) 4.13 (q, J=7.32 Hz, 1H) 1.32 (d, 6H). MS m/z (DCI) 153.0 (M+H)$^+$.

Example 16B

N-{2-[2-(3-isopropoxyphenoxy)-1,3-benzothiazol-6-yl]propyl}acetamide

The reaction was carried out using the same method as described in Example 17E except for substituting Example 16A for 4-hydroxydiphenylamine. The crude product was purified by HPLC using 5-80% acetonitrile and 0.1% trifluoroacetic acid to afford 0.045 g (48%) of the title compound. $^1$H NMR (300 MHz, DMSO-d$_6$) δ ppm 7.84 (t, J=5.70 Hz, 1H) 7.78 (d, 1H) 7.62 (d, J=8.09 Hz, 1H) 7.39 (t, J=8.27 Hz, 1H) 7.28 (dd, J=8.46, 1.84 Hz, 1H) 7.01 (t, J=2.21 Hz, 1H) 6.95 (dd, J=7.91, 2.39 Hz, 1H) 6.91 (dd, J=8.46, 1.84 Hz, 1H) 4.58-4.74 (m, 1H) 3.20 (t, 2H) 2.94 (q, J=7.23 Hz, 1H) 1.70-1.82 (m, 2H) 1.28 (d, J=5.88 Hz, 6H) 1.20 (d, J=6.99 Hz, 3H). MS m/z (DCI) 385.1 (M+H)$^+$.

Example 17

N-{2-[2-(4-anilinophenoxy)-1,3-benzothiazol-6-yl]propyl}acetamide

Example 17A 4-(2-amino-1-methyl-ethyl)-phenylamine 2-(4-Nitrophenyl)propionitrile (5.0 g, 28.38 mmoL) was dissolved in a 20% NH$_3$/methanol mixture (100 mL) and treated with Raney Nickel (24.79 g). It was then hydrogenated at 60 psi at room temperature for 4 hr. The reaction was then filtered through a nylon membrane. The filtrate was then concentrated in vacuo to give 4.26 g (100%) of the title compound. It was used without further purification. $^1$H NMR (300 MHz, CDCl$_3$) δ ppm 7.00 (d, J=8.46 Hz, 2H) 6.66 (d, J=8.09 Hz, 2H) 3.58 (s, 2H) 2.71-2.85 (m, 2H) 2.56-2.70 (m, 1H) 1.20 (d, J=6.62 Hz, 3H). MS m/z (DCI) 151.0 (M+H)$^+$.

Example 17B

N-[2-(4-aminophenyl)-propyl]-acetamide

Example 17A (1.10 g, 7.33 mmoL) was dissolved in anhydrous EtOH (24 mL) and cooled to 0° C. It was then treated with N-acetyl-N-(2-trifluoromethyl-phenyl)acetamide (1.98 g, 8.07 mmoL) and placed in the freezer for 16 hr. It was then concentrated in vacuo. The crude product was purified by flash chromatography (SiO$_2$, 100% ethyl acetate) to afford 1.20 g (85%) of the title compound. $^1$H NMR (300 MHz, CDCl$_3$) δ ppm 6.99 (d, J=8.46 Hz, 2H) 6.66 (d, J=8.46 Hz, 2H) 5.30 (s, 1H) 3.49-3.74 (m, 3H) 3.04-3.22 (m, 1H) 2.71-2.89 (m, 1H) 1.88 (s, 3H) 1.23 (d, 3H). MS m/z (DCI) 193.1 (M+H)$^+$.

Example 17C

N-[2-(2-amino-benzothiazol-6 yl)-propyl]-acetamide

Example 17B (1.20 g, 6.26 mmoL) was dissolved in HOAc (9.0 mL), treated with potassium thiocyanate (2.43 g, 25.04 mmoL), and stirred together for 20 min. Next the reaction was treated with a solution of bromine (0.32 mL, 1.00 g, 6.26 mmoL) in HOAc (6.2 mL) by slow addition over 20 min. The reaction was stirred at room temperature for 16 hr then poured into H$_2$O (125 mL). This was basified with NH$_4$OH (25 mL) and extracted with ethyl acetate (3×100 mL). The combined extracts were washed with brine (2×100 mL), dried (Na$_2$SO$_4$), and concentrated in vacuo to give 1.45 g (93%) of the title compound. The material was used without further purification. $^1$H NMR (300 MHz, DMSO-d$_6$) δ ppm 7.82 (t, J=5.70 Hz, 1H) 7.49 (d, J=1.47 Hz, 1H) 7.35 (s, 2H) 7.24 (d, J=8.46 Hz, 1H) 7.04 (dd, J=8.27, 1.65 Hz, 1H) 3.16 (t, J=6.62 Hz, 2H) 2.77-2.93 (m, 1H) 1.76 (s, 3H) 1.18 (d, J=6.25 Hz, 3H). MS m/z (DCI) 250.0 (M+H)$^+$.

Example 17D

N-[2-(2-bromo-benzothiazol-6-yl)-propyl]-acetamide t-Butylnitrite (0.960 mL, 0.832 g, 5.38 mmoL) was dissolved in anhydrous CH$_3$CN (15 mL) and cooled to 0° C. The solution was then treated with Example 17C (1.34 g, 5.38 mmoL) by portion-wise addition of the solid over 25 min. The reaction was then stirred at room temperature for 1.5 hr and then poured into 1N HCl (100 mL). This was extracted with ethyl acetate (3×100 mL). The combined extracts were washed with H$_2$O (1×100 mL) followed by brine (1×100 mL). The extracts were dried (Na$_2$SO$_4$) and concentrated in vacuo to give the crude product. The crude product was purified by flash chromatography (SiO$_2$, 100% ethyl acetate) to afford 1.18 g (70%) of the title compound. $^1$H NMR (300 MHz, CDCl$_3$) δ ppm 7.93 (d, 1H) 7.65 (d, J=1.84 Hz, 1H) 7.33 (dd, 1H) 5.37 (s, 1H) 3.57-3.74 (m, 1H) 3.22-3.37 (m, 1H) 3.02-3.19 (m, 1H) 1.87-1.93 (m, 3H) 1.34 (d, J=7.54 Hz, 3H). MS m/z (DCI) 312.9 (M+H)$^+$.

Example 17E

N-{2-[2-(4-anilinophenoxy)-1,3-benzothiazol-6-yl]propyl}acetamide

Example 17D (0.074 g, 0.238 mmoL), 4-hydroxydiphenylamine (0.048 g, 0.261 mmoL), and potassium carbonate (0.033, 0.234 mmoL) were dissolved in anhydrous dimethyl sulfoxide (0.9 mL). The mixture was then heated in the microwave at 130° C. for 30 min. H₂O (25 mL) was added to the reaction. This was extracted with dichloromethane (3×25 mL). The extracts were then washed with H₂O (4×25 mL) followed by brine (1×25 mL). They were dried (Na₂SO₄), filtered and concentrated in vacuo. The crude product was purified by flash chromatography (SiO₂, 100% ethyl acetate) to afford 0.34 g (35%) of the title compound. $^1$H NMR (300 MHz, DMSO-d₆) δ ppm 7.84 (t, J=5.33 Hz, 1H) 7.76 (s, 1H) 7.60 (d, J=8.09 Hz, 1H) 7.21-7.35 (m, 4H) 7.07-7.20 (m, 3H) 6.86 (t, J=7.17 Hz, 1H) 3.14-3.27 (m, 2H) 2.86-3.05 (m, 1H) 2.09 (s, 2H) 1.75 (s, 3H) 1.21 (t, J=7.17 Hz, 3H). MS m/z (DCI) 418.0 (M+H)⁺.

Example 18

N-(2-{2-[4-(2-naphthylamino)phenoxy]-1,3-benzothiazol-6-yl}propyl)acetamide

The reaction was carried out using the same method as described in Example 17E except for substituting N-(4-hydroxyphenyl)-2-naphthylamine for 4-hydroxydiphenylamine. The crude product was purified by flash chromatography (SiO₂, 100% ethyl acetate) to afford 0.027 g (25%) of the title compound. $^1$H NMR (300 MHz, DMSO-d₆) δ ppm 3.91-4.12 (m, 1H) 3.12-3.28 (m, 1H) 3.21 (t, 2H) 2.87-3.04 (m, 1H) 1.75 (s, 3H) 1.11-1.28 (m, 13H). MS m/z (DCI) 468.1 (M+H)⁺.

Example 19

N-(2-{2-[(6-methoxy-2-naphthyl)oxy]-1,3-benzothiazol-6-yl}propyl)acetamide

The reaction was carried out using the same method as described in Example 17E except for substituting 6-methoxy-2-naphthol for 4-hydroxydiphenylamine. The crude product was purified by flash chromatography (SiO₂, 100% ethyl acetate) to afford 0.069 g (72%) of the title compound. $^1$H NMR (300 MHz, CDCl₃) δ ppm 7.66-7.76 (m, 3H) 7.51 (d, J=1.47 Hz, 1H) 7.43 (dd, J=8.82, 2.21 Hz, 1H) 7.16-7.28 (m, 4H) 5.25-5.39 (m, 1H) 3.94 (s, 3H) 3.59-3.72 (m, 1H) 3.17-3.30 (m, 1H) 2.95-3.11 (m, 1H) 1.89 (s, 3H) 1.30 (d, 3H). MS m/z (DCI) 407.0 (M+H)⁺.

Example 20

N-(2-{2-[(7-methoxy-2-naphthyl)oxy]-1,3-benzothiazol-6-yl}propyl)acetamide

The reaction was carried out using the same method as described in Example 17E except for substituting 7-methoxy-2-naphthol for 4-hydroxydiphenylamine. The crude product was purified by flash chromatography (SiO₂, 100% ethyl acetate) to afford 0.084 g (86%) of the title compound. $^1$H NMR (300 MHz, CDCl₃) δ ppm 7.85 (d, J=8.82 Hz, 1H) 7.77 (d, J=9.19 Hz, 1H) 7.67-7.74 (m, 2H) 7.52 (d, J=1.84 Hz, 1H) 7.31 (dd, J=8.82, 2.21 Hz, 1H) 7.24 (dd, 1H) 7.11-7.20 (m, 2H) 5.30 (s, 1H) 3.93 (s, 3H) 3.60-3.72 (m, 1H) 3.17-3.31 (m, 1H) 2.93-3.10 (m, 1H) 1.90 (s, 3H) 1.31 (d, J=6.99 Hz, 3H). MS m/z (DCI) 407.2 (M+H)⁺.

Example 21

N-{2-[2-(quinolin-3-yloxy)-1,3-benzothiazol-6-yl]propyl}acetamide

Example 21A 3-hydroxyquinoline

3-Bromoquinoline (5.0 g, 24.03 mmoL) was dissolved in anhydrous ether and cooled to −78° C. It was then treated with n-butyllithium (10.57 mL, 26.43 mmoL, 2.5M in hexanes) by slow addition over 30 min. The reaction was stirred at −78° C. for 30 min then it was treated with trimethylborate (2.50 g, 24.03 mmoL) by slow addition over 10-15 min. The reaction was then allowed to stir at 0° C. for 45 min then at room temperature for 15 min. The reaction was then cooled back to −78° C. and treated with peracetic acid (5.49 g, 26.44 mmoL) and stirred at room temperature for 20 hr. The reaction was diluted with H₂O (40 mL) and solid sodium bisulfite was added until the peroxides were destroyed as indicated with peroxide test strips. The layers were separated and the aqueous layer extracted with ethyl acetate (2×50 mL). The organic layer was concentrated in vacuo and the residue was azeodried with toluene (4×50 mL). The residue was triturated with toluene and the solids were collected by vacuum filtration to give 1.43 g (41%) of the title compound. $^1$H NMR (300 MHz, DMSO-d₆) δ ppm 10.29 (s, 1H) 8.58 (d, J=2.57 Hz, 1H) 7.85-7.95 (m, 1H) 7.72-7.83 (m, 1H) 7.40-7.57 (m, 3H). MS m/z (DCI) 146.0 (M+H)⁺.

Example 21B

N-{2-[2-(quinolin-3-yloxy)-1,3-benzothiazol-6-yl]propyl}acetamide

The reaction was carried out using the same method as described in Example 17E except for substituting Example 21A for 4-hydroxydiphenylamine. The crude product was purified by flash chromatography (SiO₂, 100% ethyl acetate) to afford 0.072 g (79%) of the title compound. $^1$H NMR (300 MHz, CDCl₃) δ ppm 8.97 (d, J=2.57 Hz, 1H) 8.27 (d, J=2.94 Hz, 1H) 8.16 (d, J=8.46 Hz, 1H) 7.86 (d, J=8.09 Hz, 1H) 7.54-7.80 (m, 4H) 7.26 (d, 1H) 5.33 (s, 1H) 3.57-3.74 (m, 1H) 3.16-3.35 (m, 1H) 2.99-3.14 (m, 1H) 1.87-1.93 (m, 3H) 1.32 (d, J=6.99 Hz, 3H). MS m/z (DCI) 378.1 (M+H)⁺.

Example 22

N-(2-{2-[4-(4-isopropoxyphenoxy)phenoxy]-1,3-benzothiazol-6-yl}propyl)acetamide

Example 22A 4-(4-isopropoxyphenoxy)phenol 4,4'-Oxydiphenol (3.68 g, 0.018 mmoL) and 2-iodopropane (1.82 mL, 0.018 mmoL) were dissolved in ethanol (3 mL) and heated at reflux. It was then treated with a solution of potassium hydroxide (0.0012 g, 0.019 mmoL) dissolved in H₂O (3 mL) by addition over 10 min. The reaction was refluxed for 1 hr then it was concentrated in vacuo. The residue was dissolved in diethyl ether (50 mL) and washed with brine (1×50 mL). The organic layer was dried (MgSO₄), filtered and concentrated in vacuo. The crude product was purified by flash chromatography (SiO₂, ethyl acetate:hexanes (25:75)) to afford 1.97 g (44%) of the title compound. $^1$H NMR (300 MHz, CDCl₃) δ ppm 6.74-6.92 (m, 8H) 4.57 (s, 1H) 4.40-4.51 (m, 1H) 1.32 (d, J=5.88 Hz, 6H). MS m/z (DCI) 266 (M+NH₄)⁺.

Example 22B

N-(2-{2-[4-(4-isopropoxyphenoxy)phenoxy]-1,3-benzothiazol-6-yl}propyl)acetamide

The reaction was carried out using the same method as described in Example 17E except for substituting Example 22A for 4-hydroxydiphenylamine. The crude product was purified by flash chromatography (SiO$_2$, 100% ethyl acetate) to afford 0.044 g (38%) of the title compound. $^1$H NMR (300 MHz, CDCl$_3$) δ ppm 7.69 (d, J=8.09 Hz, 1H) 7.51 (d, J=1.47 Hz, 1H) 7.19-7.32 (m, 3H) 6.96-7.04 (m, 4H) 6.86-6.93 (m, 2H) 5.28 (s, 1H) 4.44-4.56 (m, 1H) 3.60-3.73 (m, 1H) 3.16-3.30 (m, 1H) 2.96-3.10 (m, 1H) 1.89 (s, 3H) 1.35 (d, J=6.25 Hz, 6H) 1.30 (d, 3H). MS m/z (DCI) 477.1 (M+H)$^+$.

Example 23

N-{2-[2-(3-anilinophenoxy)-1,3-benzothiazol-6-yl]propyl}acetamide

The reaction was carried out using the same method as described in Example 17E except for substituting 3-hydroxydiphenylamine for 4-hydroxydiphenylamine. The crude product was purified by flash chromatography (SiO$_2$, 100% ethyl acetate) to afford 0.053 g (73%) of the title compound. $^1$H NMR (300 MHz, CDCl$_3$) δ ppm 7.51 (d, J=1.84 Hz, 1H) 7.19-7.36 (m, 5H) 7.13 (d, J=7.72 Hz, 2H) 7.06 (t, J=2.21 Hz, 1H) 6.89-7.03 (m, 2H) 6.86 (dd, J=8.09, 1.47 Hz, 1H) 5.86 (s, 1H) 5.29 (s, 1H) 3.58-3.75 (m, 1H) 3.16-3.31 (m, 1H) 2.95-3.12 (m, 1H) 1.55-1.60 (m, 3H) 1.30 (d, J=6.99 Hz, 3H). MS m/z (DCI) 418.1 (M+H)$^+$.

Example 24

N-{2-[2-(quinolin-6-yloxy)-1,3-benzothiazol-6-yl]propyl}acetamide

The reaction was carried out using the same method as described in Example 17E except for substituting 6-hydroxyquinoline for 4-hydroxydiphenylamine. The crude product was purified by flash chromatography (SiO$_2$, 100% ethyl acetate) to afford 0.030 g (31%) of the title compound. $^1$H NMR (300 MHz, CDCl$_3$) δ ppm 8.95 (dd, J=4.23, 1.65 Hz, 1H) 8.19 (t, J=8.46 Hz, 2H) 7.86 (d, J=2.94 Hz, 1H) 7.66-7.77 (m, 2H) 7.56 (d, J=1.47 Hz, 1H) 7.46 (dd, J=8.27, 4.23 Hz, 1H) 7.26 (dd, 1H) 5.30 (s, 1H) 3.58-3.73 (m, 1H) 3.19-3.34 (m, 1H) 2.95-3.13 (m, 1H) 1.87-1.92 (m, 3H) 1.32 (d, J=6.99 Hz, 3H). MS m/z (DCI) 378.2 (M+H)$^+$.

It is understood that the foregoing detailed description and accompanying examples are merely illustrative and are not to be taken as limitations upon the scope of the invention, which is defined solely by the appended claims and their equivalents. Various changes and modifications including, but not limited to, those relating to the chemical structures, substituents, derivatives, intermediates, syntheses, formulations and/or methods of use of the invention, can be made without departing from the spirit and scope thereof.

We claim:
1. A compound of formula (I), or a pharmaceutically acceptable salt, prodrug, or salt of a prodrug thereof,

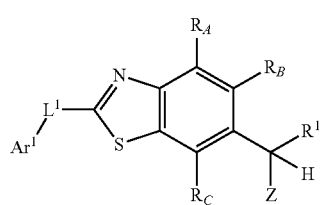

(I)

wherein
R$^1$ is hydrogen, alkyl, haloalkyl, or cycloalkyl;
L$^1$ is —CR$_x$R$_y$—, —C(O)—, —O—, or —S—; wherein each of R$_x$ and R$_y$ is independently selected from the group consisting of hydrogen, alkyl, hydroxyalkyl and haloalkyl; or R$_x$ and R$_y$ together with the carbon to which they are attached form a three to six-membered monocyclic ring selected from the group consisting of cycloalkyl and heterocycle ring;
R$_A$, R$_B$ and R$_C$ are each independently hydrogen, alkyl, halogen or haloalkyl;
Z is —CN, —OR$^2$, -alkylenyl-OR$^2$, —N(R$^3$)(R$^4$) or -alkylenyl-N(R$^3$)(R$^4$);
R$^2$, at each occurrence, is independently selected from the group consisting of hydrogen, alkyl, haloalkyl, —C(O)OR$_a$, —S(O)$_2$R$_a$, —C(O)N(R$_a$)(R$_b$), —S(O)$_2$N(R$_a$)(R$_b$), —C(O)R$_a$, -alkylenyl-OR$_a$, -alkylenyl-N(R$_a$)(R$_b$), -alkylenyl-N(R$_b$)C(O)OR$_a$, -alkylenyl-N(R$_b$)C(O)N(R$_a$)(R$_b$), -alkylenyl-N(R$_b$)C(O)R$_a$, -alkylenyl-N(R$_b$)S(O)$_2$R$_a$, -alkylenyl-C(O)OR$_a$, -alkylenyl-S(O)$_2$R$_a$, -alkylenyl-S(O)$_2$OR$_a$, -alkylenyl-S(O)$_2$N(R$_a$)(R$_b$), -alkylenyl-C(O)N(R$_a$)(R$_b$) and -alkylenyl-C(O)R$_a$;
R$^3$, at each occurrence, is independently selected from the group consisting of hydrogen, alkyl and haloalkyl;
R$^4$, at each occurrence, is independently selected from the group consisting of hydrogen, alkyl, hydroxy, alkoxy, —C(=NH)NH$_2$, —C(O)OR$_a$, —S(O)$_2$R$_a$, —C(O)N(R$_a$)(R$_b$), S(O)$_2$N(R$_a$)(R$_b$), —C(O)R$_a$, —C(O)CH$_2$C(O)R$_a$, haloalkyl, -alkylenyl-OR$_a$, -alkylenyl-N(R$_a$)(R$_b$), -alkylenyl-N(R$_b$)C(O)OR$_a$, -alkylenyl-N(R$_b$)C(O)N(R$_a$)(R$_b$), -alkylenyl-N(R$_b$)S(O)$_2$R$_a$, -alkylenyl-N(R$_b$)C(O)R$_a$, -alkylenyl-C(O)OR$_a$, -alkylenyl-S(O)$_2$R$_a$, -alkylenyl-S(O)$_2$OR$_a$, -alkylenyl-S(O)$_2$N(R$_a$)(R$_b$), -alkylenyl-C(O)N(R$_a$)(R$_b$) and -alkylenyl-C(O)R$_a$,
Ar$^1$ is phenyl or monocyclic heteroaryl, each of which is optionally fused to a phenyl or a monocyclic, five- or six-membered ring selected from the group consisting of cycloalkyl, cycloalkenyl, heterocycle and heteroaryl, and each Ar$^1$ is independently unsubstituted or substituted with 1, 2, 3 or 4 substituents independently selected from the group consisting of alkyl, alkenyl, —CN, —NO$_2$, halogen, —OR$^6$, —O—N=CH(R$^5$), —OC(O)R$^5$, —OC(O)N(R$^7$)(R$^6$), —OC(O)OR$^5$, —OS(O)$_2$R$^5$, —SR$^6$, —S(O)R$^5$, —S(O)$_2$R$^5$, —S(O)$_2$OR$^6$, —S(O)$_2$N(R$^7$)(R$^6$), —C(O)R$^6$, —C(O)N(R$^7$)(R$^6$), —C(O)OR$^6$, —C(O)N(R$^7$)(R$^6$), —N(R$^7$)(R$^6$), —N(H)—N=CH(R$^5$), —N(R)C(O)R$^6$, —N(R)C(O)OR$^6$, —N(R)S(O)$_2$R$^6$, —N(R)C(O)N(R$^7$)(R$^6$), —N(R)S(O)$_2$N(R$^7$)(R$^6$), —R$^8$, haloalkyl, cyanoalkyl, nitroalkyl, hydroxyalkyl, alkoxyalkyl, haloalkoxyalkyl, -alkylenyl-OC(O)R$^5$, -alkylenyl-OC(O)N(R$^7$)(R$^6$), -alkylenyl-OC(O)OR$^5$, -alkylenyl-OS(O)$_2$R$^5$, -alkylenyl-SR$^6$, -alkylenyl-S(O)R$^5$, -alkylenyl-S(O)$_2$R$^5$, -alkylenyl-S(O)$_2$OR$^6$, -alkylenyl-S(O)$_2$N(R$^7$)(R$^6$), -alkylenyl-C(O)R$^6$, -alkylenyl-C(O)N(R$^7$)(R$^6$), -alkylenyl-C(O)OR$^6$, -alkylenyl-C(O)N(R$^7$)(R$^6$), -alkylenyl-N(R$^7$)(R$^6$), -alkylenyl-N(R$^7$)C(O)R$^5$, -alkylenyl-N(R$^7$)C(O)OR$^5$, -alkylenyl-N(R$^7$)S(O)$_2$R$^5$, -alkylenyl-N(R)C(O)N(R$^7$)(R$^6$), -alkylenyl-N(R$^7$)S(O)$_2$N(R$^7$)(R$^6$), and -alkylenyl-R$^8$;
R$^5$, at each occurrence, is independently selected from the group consisting of alkyl, alkenyl, haloalkyl, alkoxyalkyl, haloalkoxyalkyl, —R$^8$, and -alkylenyl-R$^8$;
R$^6$, at each occurrence, is independently selected from the group consisting of hydrogen, alkyl, alkenyl, haloalkyl, alkoxyalkyl, haloalkoxyalkyl, —R$^8$, and -alkylenyl-R$^8$;

R[7], at each occurrence, is independently selected from the group consisting of hydrogen, alkyl, arylalkyl, haloalkyl, and heteroarylalkyl;

R[8], at each occurrence, is independently selected from the group consisting of aryl, heteroaryl, heterocycle, cycloalkyl and cycloalkenyl;

the cycloalkyl, cycloalkenyl, aryl, heteroaryl, heterocycle, aryl moiety of the arylalkyl, and the heteroaryl moiety of the heteroarylalkyl represented by R[7] and R[8], are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —OR$_a$, —OC(O)R$_a$, —OC(O)OR$_a$, —OS(O)$_2$R$_a$, —S(alkyl), —S(O)alkyl, —S(O)$_2$alkyl, —S(O)$_2$OR$_a$, —S(O)$_2$NR$_a$R$_b$, —C(O)R$_a$, —C(O)NR$_a$R$_b$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)OR$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$;

R$_a$ at each occurrence is independently selected from the group consisting of hydrogen, alkyl, alkenyl and haloalkyl, and R$_b$ at each occurrence is independently selected from the group consisting of hydrogen and alkyl.

2. The compound of claim 1 or a pharmaceutically acceptable salt, prodrug, or salt of a prodrug thereof, wherein Ar[1] is unsubstituted phenyl or unsubstituted pyridinyl, each of which is fused to an unsubstituted phenyl or unsubstituted pyridinyl; or Ar[1] is a group of formula (a), (b), (c) or (d)

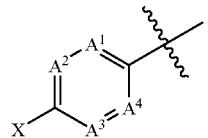

(a)

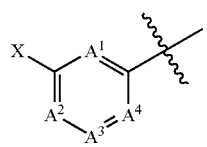

(b)

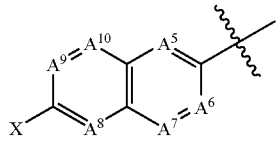

(c)

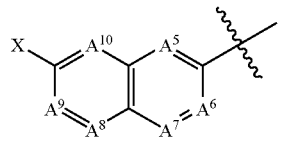

(d)

A[1], A[2], A[3] and A[4] are —C(R$_E$)—, or one or two of A[1], A[2], A[3] and A[4] is N and the others are —C(R$_E$)—, A[5], A[6], and A[7] are —C(R$_F$)—, or one or two of A[5], A[6], and A[7] is N and the others are —C(R$_F$)—, A[8], A[9], and A[10] are —C(R$_F$)—, or one or two of A[8], A[9], and A[10] is N and the others are —C(R$_F$)—, wherein R$_E$ and R$_F$, at each occurrence, are each independently selected from the group consisting of hydrogen, alkyl, alkenyl, CN, NO$_2$, halogen, hydroxy, alkoxy, —NH$_2$—N(H)alkyl, —N(alkyl)$_2$-SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;

X is —OR[6] or —N(R[7])(R[6]); and

L[1] is —O—.

3. The compound of claim 1 or a pharmaceutically acceptable salt, prodrug, or salt of a prodrug thereof, wherein Ar[1] is unsubstituted phenyl or unsubstituted pyridinyl, each of which is fused to an unsubstituted phenyl or unsubstituted pyridinyl; or Ar[1] is a group of formula (a), (b), (c) or (d)

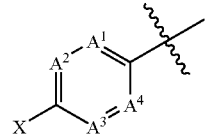

(a)

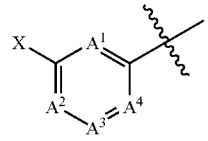

(b)

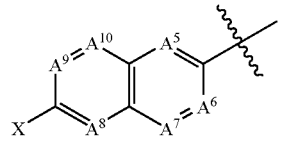

(c)

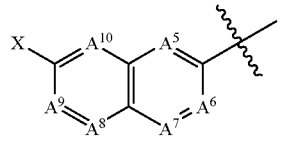

(d)

A[1], A[2], A[3] and A[4] are —C(R$_E$)—,

A[5], A[6], and A[7] are —C(R$_F$)—,

A[8], A[9], and A[10] are —C(R$_F$)—, wherein R$_E$ and R$_F$, at each occurrence, are each independently selected from the group consisting of hydrogen, —I, —Br, —Cl, and —F;

R$_A$, R$_B$ and R$_C$ are hydrogen;

L[1] is —O—

X is —OR[6] wherein R[6] is selected from the group consisting of C$_1$-C$_6$ alkyl and aryl, or X is —N(R[7])(R[6]) wherein R[7] is hydrogen and R[6] is aryl;

$R^1$ is $C_1$-$C_6$ alkyl or $C_1$-$C_6$ haloalkyl; and

Z is —CN, —$OR^2$, —N($R^3$)($R^4$), or —$C_1$-$C_6$ alkylenyl-N($R^3$)($R^4$); wherein $R^2$ is hydrogen or —C(O)$R_a$ wherein $R_a$, is $C_1$-$C_6$ alkyl;

$R^3$ is hydrogen; and $R^4$ is hydrogen, —C(O)$R_a$ wherein $R_a$ is $C_1$-$C_6$ alkyl, or $R^4$ is —C(O)N($R_a$)($R_b$) wherein $R_a$ is hydrogen and $R_b$ is hydrogen or $C_1$-$C_6$ alkyl.

4. The compound of claim 2 or a pharmaceutically acceptable salt, prodrug, or salt of a prodrug thereof, wherein $Ar^1$ is formula (a),

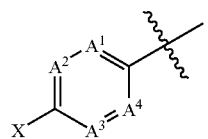

(a)

$A^1$, $A^2$, $A^3$ and $A^4$ are —C($R_E$)—, or one of $A^1$, $A^2$, $A^3$ and $A^4$ is N and the others are —C($R_E$)—;

X is —$OR^6$ wherein $R^6$ is selected from the group consisting of $C_1$-$C_6$ alkyl and aryl;

$L^1$ is —O—;

$R^1$ is $C_1$-$C_6$ alkyl or $C_1$-$C_6$ haloalkyl; and

Z is —CN, —$OR^2$, —N($R^3$)($R^4$), or —$C_1$-$C_6$ alkylenyl-N($R^3$)($R^4$); wherein $R^2$ is hydrogen or —C(O)$R_a$ wherein $R_a$ is $C_1$-$C_6$ alkyl;

$R^3$ is hydrogen; and $R^4$ is hydrogen, —C(O)$R_a$ wherein $R_a$ is $C_1$-$C_6$ alkyl, or $R^4$ is —C(O)N($R_a$)($R_b$) wherein $R_a$ is hydrogen and $R_b$ is hydrogen or $C_1$-$C_6$ alkyl.

5. The compound of claim 2 or a pharmaceutically acceptable salt, prodrug, or salt of a prodrug thereof, wherein $Ar^1$ is formula (a),

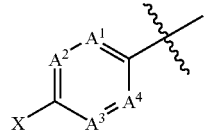

(a)

$A^1$, $A^2$, $A^3$ and $A^4$ are —C($R_E$)—, or one of $A^1$, $A^2$, $A^3$ and $A^4$ is N and the others are —C($R_E$)—; wherein each $R_E$ is independently selected from the group consisting of hydrogen, —I, —Br, —Cl, and —F;

$R_A$, $R_B$ and $R_C$ are hydrogen;

X is —$OR^6$ wherein $R^6$ is selected from the group consisting of methyl, isopropyl, phenyl, and naphthyl, wherein phenyl and naphthyl are independently unsubstituted or substituted with one isopropoxy;

$L^1$ is —O—;

$R^1$ is methyl; and

Z is —CN, —$OR^2$, —N($R^3$)($R^4$), or —$CH_2$—N($R^3$)($R^4$); wherein $R^2$ is hydrogen or —C(O)(methyl);

$R^3$ is hydrogen; and $R^4$ is hydrogen, —C(O)(methyl), or —C(O)N($R_a$)($R_b$) wherein $R_a$ is hydrogen and $R_b$ is hydrogen or methyl.

6. The compound of claim 5 selected from the group consisting of:

1-[2-(4-phenoxyphenoxy)-1,3-benzothiazol-6-yl]ethanol;

N-{1-[2-(4-phenoxyphenoxy)-1,3-benzothiazol-6-yl]ethyl}acetamide;

1-[2-(4-phenoxyphenoxy)-1,3-benzothiazol-6-yl]ethyl acetate;

1-[2-(4-phenoxyphenoxy)-1,3-benzothiazol-6-yl]ethanamine;

2-[2-(4-phenoxyphenoxy)-1,3-benzothiazol-6-yl]propanenitrile;

2-[2-(4-phenoxyphenoxy)-1,3-benzothiazol-6-yl]propan-1-amine;

N-{1-[2-(4-phenoxyphenoxy)-1,3-benzothiazol-6-yl]ethyl}urea;

N-{2-[2-(4-phenoxyphenoxy)-1,3-benzothiazol-6-yl]propyl}acetamide;

2-[2-(4-isopropoxyphenoxy)-1,3-benzothiazol-6-yl]propanenitrile;

2-[2-(4-isopropoxyphenoxy)-1,3-benzothiazol-6-yl]propan-1-amine;

N-{2-[2-(4-isopropoxyphenoxy)-1,3-benzothiazol-6-yl]propyl}acetamide; and

N-(2-{2-[4-(4-isopropoxyphenoxy)phenoxy]-1,3-benzothiazol-6-yl}propyl)acetamide or a pharmaceutically acceptable salt, prodrug, or salt of a prodrug thereof.

7. The compound of claim 2 or a pharmaceutically acceptable salt, prodrug, or salt of a prodrug thereof, wherein $Ar^1$ is formula (a),

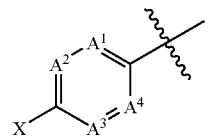

(a)

$A^1$, $A^2$, $A^3$ and $A^4$ are —C($R_E$)—, or one of $A^1$, $A^2$, $A^3$ and $A^4$ is N and the others are —C($R_E$)—;

X is —N($R^6$)($R^7$) wherein $R^7$ is hydrogen and $R^6$ is aryl;

$L^1$ is —O—;

$R^1$ is $C_1$-$C_6$ alkyl or $C_1$-$C_6$ haloalkyl; and

Z is —CN, —$OR^2$, —N($R^3$)($R^4$), or —$C_1$-$C_6$ alkylenyl-N($R^3$)($R^4$); wherein $R^2$ is hydrogen or —C(O)$R_a$ wherein $R_a$, is $C_1$-$C_6$ alkyl;

$R^3$ is hydrogen; and $R^4$ is hydrogen, —C(O)$R_a$ wherein $R_a$ is $C_1$-$C_6$ alkyl, or —C(O)N(R)($R_b$) wherein $R_a$ is hydrogen and $R_b$ is hydrogen or $C_1$-$C_6$ alkyl.

8. The compound of claim 2 or a pharmaceutically acceptable salt, prodrug, or salt of a prodrug thereof, wherein $Ar^1$ is formula (a),

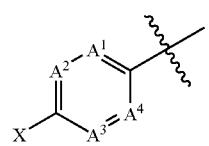

(a)

$A^1$, $A^2$, $A^3$ and $A^4$ are —C($R_E$)—, or one of $A^1$, $A^2$, $A^3$ and $A^4$ is N and the others are —C($R_E$)—;

wherein each $R_E$ is independently selected from the group consisting of hydrogen, —I, —Br, —Cl, and —F;

X is —N(R⁶)(R⁷) wherein R⁷ is hydrogen and R⁶ is phenyl or naphthyl wherein each R⁶ is independently unsubstituted or substituted with one isopropoxy;

R$_A$, R$_B$ and R$_C$ are hydrogen;

L¹ is —O—;

R¹ is methyl; and

Z is —CN, —OR², —N(R³)(R⁴), or —CH₂—N(R³)(R⁴); wherein

R² is hydrogen or —C(O)(methyl);

R³ is hydrogen; and

R⁴ is hydrogen, —C(O)(methyl), or —C(O)N(R$_a$)(R$_b$) wherein R$_a$ is hydrogen and R$_b$ is hydrogen or methyl.

9. The compound of claim 8 selected from the group consisting of:

N-{2-[2-(4-anilinophenoxy)-1,3-benzothiazol-6-yl]propyl}acetamide; and

N-(2-{2-[4-(2-naphthylamino)phenoxy]-1,3-benzothiazol-6-yl}propyl)acetamide or a pharmaceutically acceptable salt, prodrug, or salt of a prodrug thereof.

10. The compound of claim 2 or a pharmaceutically acceptable salt, prodrug, or salt of a prodrug thereof, wherein Ar¹ is formula (b),

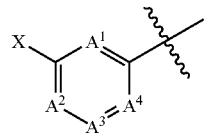

(b)

A¹, A², A³ and A⁴ are —C(R$_E$)—, or one of A¹, A², A³ and A⁴ is N and the others are —C(R$_E$)—;

X is —OR⁶ wherein R⁶ is selected from the group consisting of C₁-C₆ alkyl and aryl;

L¹ is —O—;

R¹ is C₁-C₆ alkyl or C₁-C₆ haloalkyl; and

Z is —CN, —OR², —N(R³)(R⁴), or —C₁-C₆ alkylenyl-N(R³)(R⁴); wherein

R² is hydrogen or —C(O)R$_a$ wherein R$_a$, is C₁-C₆ alkyl;

R³ is hydrogen; and

R⁴ is hydrogen, —C(O)R$_a$ wherein R$_a$ is C₁-C₆ alkyl, or R⁴ is —C(O)N(R$_a$)(R$_b$) wherein R$_a$ is hydrogen and R$_b$ is hydrogen or C₁-C₆ alkyl.

11. The compound of claim 2 or a pharmaceutically acceptable salt, prodrug, or salt of a prodrug thereof, wherein Ar¹ is formula (b),

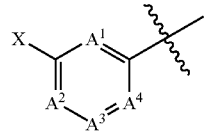

(b)

A¹, A², A³ and A⁴ are —C(R$_E$)—, or one of A¹, A², A³ and A⁴ is N and the others are —C(R$_E$)—; wherein each R$_E$ is independently selected from the group consisting of hydrogen, —I, —Br, —Cl, and —F;

R$_A$, R$_B$ and R$_C$ are hydrogen;

X is —OR⁶ wherein R⁶ is selected from the group consisting of methyl, isopropyl, phenyl and naphthyl, wherein the phenyl and the naphthyl are independently unsubstituted or substituted with one isopropoxy;

L¹ is —O—;

R¹ is methyl; and

Z is —CN, —OR², —N(R³)(R⁴), or —CH₂—N(R³)(R⁴); wherein

R² is hydrogen or —C(O)(methyl);

R³ is hydrogen; and

R⁴ is hydrogen, —C(O)(methyl), or —C(O)N(R$_a$)(R$_b$) wherein R$_a$ is hydrogen and R$_b$ is hydrogen or methyl.

12. The compound of claim 11 selected from the group consisting of:

N-{2-[2-(3-phenoxyphenoxy)-1,3-benzothiazol-6-yl]propyl}acetamide; and

N-{2-[2-(3-isopropoxyphenoxy)-1,3-benzothiazol-6-yl]propyl}acetamide;

or a pharmaceutically acceptable salt, prodrug, or salt of a prodrug thereof.

13. The compound of claim 2 or a pharmaceutically acceptable salt, prodrug, or salt of a prodrug thereof, wherein Ar¹ is formula (b),

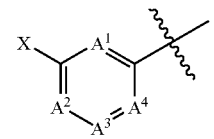

(b)

A¹, A², A³ and A⁴ are —C(R$_E$)—, or one of A¹, A², A³ and A⁴ is N and the others are —C(R$_E$)—;

X is —N(R⁶)(R⁷) wherein R⁷ is hydrogen and R⁶ is aryl;

L¹ is —O—;

R¹ is C₁-C₆ alkyl or C₁-C₆ haloalkyl; and

Z is —CN, —OR², —N(R³)(R⁴), or —C₁-C₆ alkylenyl-N(R³)(R⁴); wherein

R² is hydrogen or —C(O)R$_a$ wherein R$_a$, is C₁-C₆ alkyl;

R³ is hydrogen; and

R⁴ is hydrogen, —C(O)R$_a$ wherein R$_a$ is C₁-C₆ alkyl, or R⁴ is —C(O)N(R$_a$)(R$_b$) wherein R$_a$ is hydrogen and R$_b$ is hydrogen or C₁-C₆ alkyl.

14. The compound of claim 2 or a pharmaceutically acceptable salt, prodrug, or salt of a prodrug thereof, wherein Ar¹ is formula (b),

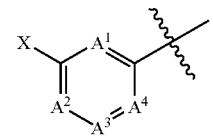

(b)

A¹, A², A³ and A⁴ are —C(R$_E$)—, or one of A¹, A², A³ and A⁴ is N and the others are —C(R$_E$)—; wherein each R$_E$ is independently selected from the group consisting of hydrogen, —I, —Br, —Cl, and —F;

R$_A$, R$_B$ and R$_C$ are hydrogen;

X is —N(R⁶)(R⁷) wherein R⁷ is hydrogen and R⁶ is phenyl or naphthyl, wherein each R⁶ is independently unsubstituted or substituted with one isopropoxy;

L¹ is —O—;

R¹ is methyl; and

Z is —CN, —OR², —N(R³)(R⁴), or —CH₂—N(R³)(R⁴); wherein

R² is hydrogen or —C(O)(methyl);

R³ is hydrogen; and $R^4$ is hydrogen, —C(O)(methyl), or —C(O)N($R_a$)($R_b$) wherein $R_a$ is hydrogen and $R_b$ is hydrogen or methyl.

15. The compound of claim 14 is N-{2-[2-(3-anilinophenoxy)-1,3-benzothiazol-6-yl]propyl}acetamide or a pharmaceutically acceptable salt, prodrug, or salt of a prodrug thereof.

16. The compound of claim 2 or a pharmaceutically acceptable salt, prodrug, or salt of a prodrug thereof, wherein
$Ar^1$ is formula (c) or (d),

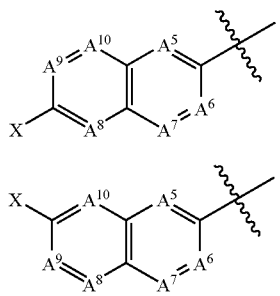

$A^5$, $A^6$, and $A^7$ are —C($R_F$)—, or one of $A^5$, $A^6$, and $A^7$ is N and the others are —C($R_F$)—,
$A^8$, $A^9$, and $A^{10}$ are —C($R_F$)—, or one of $A^8$, $A^9$, and $A^{10}$ is N and the others are —C($R_F$)—;
X is $OR^6$ wherein $R^6$ is $C_1$-$C_6$ alkyl or aryl, or —N($R^6$)($R^7$) wherein $R^7$ is hydrogen and $R^6$ is aryl;
$L^1$ is —O—;
$R^1$ is $C_1$-$C_6$ alkyl or $C_1$-$C_6$ haloalkyl; and
Z is —CN, —$OR^2$, —N($R^3$)($R^4$), or —$C_1$-$C_6$ alkylenyl-N($R^3$)($R^4$); wherein
$R^2$ is hydrogen or —C(O)$R_a$ wherein $R_a$ is $C_1$-$C_6$ alkyl;
$R^3$ is hydrogen; and
$R^4$ is hydrogen, —C(O)$R_a$ wherein $R_a$ is $C_1$-$C_6$ alkyl, or $R^4$ is —C(O)N($R_a$)($R_b$) wherein $R_a$ is hydrogen and $R_b$ is hydrogen or $C_1$-$C_6$ alkyl.

17. The compound of claim 2 or a pharmaceutically acceptable salt, prodrug, or salt of a prodrug thereof, wherein
$Ar^1$ is formula (c) or (d),

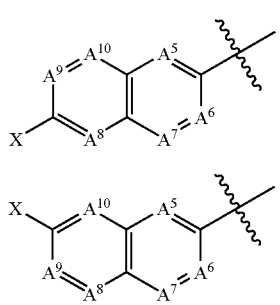

$A^5$, $A^6$, and $A^7$ are —C($R_F$)—, or one of $A^5$, $A^6$, and $A^7$ is N and the others are —C($R_F$)—,
$A^8$, $A^9$, and $A^{10}$ are —C($R_F$)—, or one of $A^8$, $A^9$, and $A^{10}$ is N and the others are —C($R_F$)—,
$R_F$, at each occurrence, are each independently selected from the group consisting of hydrogen, —I, —Br, —Cl and —F;
$R_A$, $R_B$ and $R_C$ are hydrogen;
X is $OR^6$ wherein $R^6$ is selected from the group consisting of methyl, isopropyl, phenyl and naphthyl, wherein the phenyl and naphthyl are independently unsubstituted or substituted with one isopropoxy; or X is —N($R^6$)($R^7$) wherein $R^7$ is hydrogen and $R^6$ is phenyl or naphthyl, wherein the phenyl and naphthyl are independently unsubstituted or substituted with one isopropoxy;
$L^1$ is —O—;
$R^1$ is methyl; and
Z is —CN, —$OR^2$, —N($R^3$)($R^4$), or —$CH_2$—N($R^3$)($R^4$); wherein
$R^2$ is hydrogen or —C(O)(methyl);
$R^3$ is hydrogen; and
$R^4$ is hydrogen, —C(O)(methyl), or —C(O)N($R_a$)($R_b$) wherein $R_a$ is hydrogen and $R_b$ is hydrogen or methyl.

18. The compound of claim 17 selected from the group consisting of:
N-(2-{2-[(6-methoxy-2-naphthyl)oxy]-1,3-benzothiazol-6-yl}propyl)acetamide; and
N-(2-{2-[(7-methoxy-2-naphthyl)oxy]-1,3-benzothiazol-6-yl}propyl)acetamide; or a pharmaceutically acceptable salt, prodrug, or salt of a prodrug thereof.

19. The compound of claim 2 or a pharmaceutically acceptable salt, prodrug, or salt of a prodrug thereof, wherein
$Ar^1$ is unsubstituted phenyl or unsubstituted pyridinyl, each of which is fused to an unsubstituted phenyl or unsubstituted pyridinyl;
$L^1$ is —O—;
$R^1$ is $C_1$-$C_6$ alkyl or $C_1$-$C_6$ haloalkyl; and
Z is —CN, —$OR^2$, —N($R^3$)($R^4$), or —$C_1$-$C_6$ alkylenyl-N($R^3$)($R^4$); wherein
$R^2$ is hydrogen or —C(O)$R_a$ wherein $R_a$ is $C_1$-$C_6$ alkyl;
$R^3$ is hydrogen; and
$R^4$ is hydrogen, —C(O)$R_a$ wherein $R_a$ is $C_1$-$C_6$ alkyl, or $R^4$ is —C(O)N($R_a$)($R_b$) wherein $R_a$ is hydrogen and $R_b$ is hydrogen or $C_1$-$C_6$ alkyl.

20. The compound of claim 2 or a pharmaceutically acceptable salt, prodrug, or salt of a prodrug thereof, wherein
$Ar^1$ is unsubstituted phenyl or unsubstituted pyridinyl, each of which is fused to an unsubstituted phenyl or unsubstituted pyridinyl;
$L^1$ is —O—;
$R_A$, $R_B$ and $R_C$ are hydrogen;
$R^1$ is methyl; and
Z is —CN, —$OR^2$, —N($R^3$)($R^4$), or —$CH_2$—N($R^3$)($R^4$); wherein
$R^2$ is hydrogen or —C(O)(methyl);
$R^3$ is hydrogen; and
$R^4$ is hydrogen, —C(O)(methyl), or —C(O)N($R_a$)($R_b$) wherein $R_a$ is hydrogen and $R_b$ is hydrogen or methyl.

21. The compound of claim 20 selected from the group consisting of:
N-{2-[2-(2-naphthyloxy)-1,3-benzothiazol-6-yl]propyl}acetamide;
N-{2-[2-(quinolin-3-yloxy)-1,3-benzothiazol-6-yl]propyl}acetamide; and
N-{2-[2-(quinolin-6-yloxy)-1,3-benzothiazol-6-yl]propyl}acetamide or a pharmaceutically acceptable salt, prodrug, or salt of a prodrug thereof.

22. A method of treating metabolic syndrome in a mammal comprising administering a therapeutically effective amount of a compound of claim 1.

23. A method of treating type II diabetes in a mammal comprising administering a therapeutically effective amount of a compound of claim 1.

24. A method of treating obesity in a mammal comprising administering a therapeutically effective amount of a compound of claim 1.

25. A pharmaceutical composition comprising a therapeutically effective amount of a compound of claim 1 in combination with a pharmaceutically acceptable carrier.

* * * * *